US010076258B2

(12) United States Patent
Thakur et al.

(10) Patent No.: US 10,076,258 B2
(45) Date of Patent: Sep. 18, 2018

(54) CARDIAC MAPPING USING LATENCY INTERPOLATION

(71) Applicant: BOSTON SCIENTIFIC SCIMED, INC., Maple Grove, MN (US)

(72) Inventors: Pramodsingh Hirasingh Thakur, Woodbury, MN (US); Barun Maskara, Blaine, MN (US); Shibaji Shome, Arden Hills, MN (US); Allan C. Shuros, St. Paul, MN (US); Shantha Arcot-Krishnamurthy, Renton, WA (US); Sunipa Saha, Shoreview, MN (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 557 days.

(21) Appl. No.: 14/528,539

(22) Filed: Oct. 30, 2014

(65) Prior Publication Data

US 2015/0126840 A1     May 7, 2015

Related U.S. Application Data

(60) Provisional application No. 61/899,033, filed on Nov. 1, 2013.

(51) Int. Cl.
*A61B 5/0402* (2006.01)
*A61B 5/042* (2006.01)
(Continued)

(52) U.S. Cl.
CPC ........ *A61B 5/0422* (2013.01); *A61B 5/04028* (2013.01); *A61B 5/0452* (2013.01);
(Continued)

(58) Field of Classification Search
CPC .......................... A61B 5/0422; A61B 18/1492
See application file for complete search history.

(56) References Cited

U.S. PATENT DOCUMENTS

| 4,433,380 A | 2/1984 | Abele et al. |
| 4,690,152 A | 9/1987 | Juncosa |

(Continued)

FOREIGN PATENT DOCUMENTS

| EP | 1190671 A2 | 3/2002 |
| EP | 2258263 B1 | 8/2012 |

(Continued)

OTHER PUBLICATIONS

Faes, L., et. al. Principal Component Analysis and Cluster Analysis for Measuring the Local Organization of Human Atrial Fibrillation. Med. Biol. Eng. Comput., 39(6): 656-663, 2001.

(Continued)

*Primary Examiner* — Michael D Abreu
(74) *Attorney, Agent, or Firm* — Faegre Baker Daniels LLP

(57) ABSTRACT

Medical devices and methods for using medical devices are disclosed. An example mapping medical device may include a catheter shaft with a plurality of electrodes. The plurality of electrodes may include a first pair of electrodes, a second pair of electrodes, a third pair of electrodes and a fourth pair of electrodes. The mapping medical device may further include a processor, wherein the processor may be configured to determine a first latency between the first pair of electrodes, determine a second latency between the second pair of electrodes, determine a third latency between the third pair of electrodes, determine a fourth latency between the fourth pair of electrodes, and determine a target signal by interpolating the first latency, the second latency, the third latency and the fourth latency.

20 Claims, 13 Drawing Sheets

(51) Int. Cl.
  *A61B 5/00* (2006.01)
  *A61B 18/14* (2006.01)
  *A61B 5/0452* (2006.01)
  *A61B 5/0464* (2006.01)
  *A61B 18/00* (2006.01)
  *A61N 1/06* (2006.01)

(52) U.S. Cl.
  CPC .......... *A61B 5/0464* (2013.01); *A61B 5/6852* (2013.01); *A61B 18/1492* (2013.01); *A61B 5/6858* (2013.01); *A61B 5/7278* (2013.01); *A61B 2018/0016* (2013.01); *A61B 2018/00267* (2013.01); *A61B 2018/00351* (2013.01); *A61B 2018/00577* (2013.01); *A61B 2018/1467* (2013.01); *A61B 2018/1475* (2013.01); *A61B 2562/0209* (2013.01); *A61N 1/06* (2013.01)

(56) References Cited

U.S. PATENT DOCUMENTS

| | | |
|---|---|---|
| 5,254,088 A | 10/1993 | Lundquist et al. |
| 5,383,874 A | 1/1995 | Jackson et al. |
| 5,485,849 A | 1/1996 | Panescu et al. |
| 5,487,391 A | 1/1996 | Panescu |
| 5,494,042 A | 2/1996 | Panescu et al. |
| 5,527,292 A | 6/1996 | Adams et al. |
| 5,546,940 A | 8/1996 | Panescu et al. |
| 5,577,509 A | 11/1996 | Panescu et al. |
| 5,582,609 A | 12/1996 | Swanson et al. |
| 5,595,183 A | 1/1997 | Swanson et al. |
| 5,598,848 A | 2/1997 | Swanson et al. |
| 5,601,088 A | 2/1997 | Swanson et al. |
| 5,605,157 A | 2/1997 | Panescu et al. |
| 5,609,157 A | 3/1997 | Panescu et al. |
| 5,630,425 A | 5/1997 | Panescu et al. |
| 5,647,870 A | 7/1997 | Kordis et al. |
| 5,657,755 A | 8/1997 | Desai |
| 5,687,737 A | 11/1997 | Branham et al. |
| 5,688,267 A | 11/1997 | Panescu et al. |
| 5,702,386 A | 12/1997 | Stern et al. |
| 5,711,305 A | 1/1998 | Swanson et al. |
| 5,722,402 A | 3/1998 | Swanson et al. |
| 5,722,403 A | 3/1998 | McGee et al. |
| 5,722,416 A | 3/1998 | Swanson et al. |
| 5,732,698 A | 3/1998 | Swanson et al. |
| 5,735,846 A | 4/1998 | Panescu et al. |
| 5,740,808 A | 4/1998 | Panescu et al. |
| 5,752,518 A | 5/1998 | McGee et al. |
| 5,755,715 A | 5/1998 | Stern et al. |
| 5,769,847 A | 6/1998 | Panescu et al. |
| 5,792,064 A | 8/1998 | Panescu et al. |
| 5,795,303 A | 8/1998 | Swanson et al. |
| 5,797,903 A | 8/1998 | Swanson et al. |
| 5,797,905 A | 8/1998 | Fleischman et al. |
| 5,810,802 A | 9/1998 | Panescu et al. |
| 5,830,213 A | 11/1998 | Panescu et al. |
| 5,833,621 A | 11/1998 | Panescu et al. |
| 5,836,874 A | 11/1998 | Swanson et al. |
| 5,840,076 A | 11/1998 | Swanson et al. |
| 5,846,238 A | 12/1998 | Jackson et al. |
| 5,846,239 A | 12/1998 | Swanson et al. |
| 5,848,969 A | 12/1998 | Panescu et al. |
| 5,853,409 A | 12/1998 | Swanson et al. |
| 5,853,411 A | 12/1998 | Whayne et al. |
| 5,868,680 A * | 2/1999 | Steiner ................ A61B 5/0464 600/5 |
| 5,868,736 A | 2/1999 | Swanson et al. |
| 5,871,483 A | 2/1999 | Jackson et al. |
| 5,876,336 A | 3/1999 | Swanson et al. |
| 5,879,348 A | 3/1999 | Owens et al. |
| 5,891,136 A | 4/1999 | McGee et al. |
| 5,904,651 A | 5/1999 | Swanson et al. |
| 5,904,680 A | 5/1999 | Kordis et al. |
| 5,906,614 A | 5/1999 | Stern et al. |
| 5,908,445 A | 6/1999 | Whayne et al. |
| 5,911,739 A | 6/1999 | Kordis et al. |
| 5,916,163 A | 6/1999 | Panescu et al. |
| 5,925,038 A | 7/1999 | Panescu et al. |
| 5,928,228 A | 7/1999 | Kordis et al. |
| 5,935,079 A | 8/1999 | Swanson et al. |
| 5,941,251 A | 8/1999 | Panescu et al. |
| 5,954,661 A | 9/1999 | Greenspon et al. |
| 5,954,662 A | 9/1999 | Swanson et al. |
| 5,961,513 A | 10/1999 | Swanson et al. |
| 5,968,040 A | 10/1999 | Swanson et al. |
| 6,014,581 A | 1/2000 | Whayne et al. |
| 6,014,590 A | 1/2000 | Whayne et al. |
| 6,022,346 A | 2/2000 | Panescu et al. |
| 6,030,379 A | 2/2000 | Panescu et al. |
| 6,030,382 A | 2/2000 | Fleischman et al. |
| 6,035,226 A | 3/2000 | Panescu |
| 6,047,218 A | 4/2000 | Whayne et al. |
| 6,049,732 A | 4/2000 | Panescu et al. |
| 6,053,912 A | 4/2000 | Panescu et al. |
| 6,056,745 A | 5/2000 | Panescu et al. |
| 6,070,094 A | 5/2000 | Swanson et al. |
| 6,071,278 A | 6/2000 | Panescu et al. |
| 6,076,012 A | 6/2000 | Swanson et al. |
| 6,086,532 A | 7/2000 | Panescu et al. |
| 6,095,150 A | 8/2000 | Panescu et al. |
| 6,101,409 A | 8/2000 | Swanson et al. |
| 6,101,410 A | 8/2000 | Panescu et al. |
| 6,106,460 A | 8/2000 | Panescu et al. |
| 6,106,522 A | 8/2000 | Fleischman et al. |
| 6,113,591 A | 9/2000 | Whayne et al. |
| 6,115,626 A | 9/2000 | Whayne et al. |
| 6,123,702 A | 9/2000 | Swanson et al. |
| 6,129,669 A | 10/2000 | Panescu et al. |
| 6,129,724 A | 10/2000 | Fleischman et al. |
| 6,162,184 A | 12/2000 | Swanson et al. |
| 6,165,169 A | 12/2000 | Panescu et al. |
| 6,171,306 B1 | 1/2001 | Swanson et al. |
| 6,179,835 B1 | 1/2001 | Panescu et al. |
| 6,183,468 B1 | 2/2001 | Swanson et al. |
| 6,188,924 B1 | 2/2001 | Swanson et al. |
| 6,192,266 B1 | 2/2001 | Dupree et al. |
| 6,197,021 B1 | 3/2001 | Panescu et al. |
| 6,206,831 B1 | 3/2001 | Suorsa et al. |
| 6,216,043 B1 | 4/2001 | Swanson et al. |
| 6,221,013 B1 | 4/2001 | Panescu et al. |
| 6,226,542 B1 | 5/2001 | Reisfeld |
| 6,233,491 B1 | 5/2001 | Kordis et al. |
| 6,245,061 B1 | 6/2001 | Panescu et al. |
| 6,245,065 B1 | 6/2001 | Panescu et al. |
| 6,256,540 B1 | 7/2001 | Panescu et al. |
| 6,289,239 B1 | 9/2001 | Panescu et al. |
| 6,293,943 B1 | 9/2001 | Panescu et al. |
| 6,301,496 B1 | 10/2001 | Reisfeld |
| 6,330,473 B1 | 12/2001 | Swanson et al. |
| 6,353,751 B1 | 3/2002 | Swanson et al. |
| 6,370,435 B2 | 4/2002 | Panescu et al. |
| 6,389,311 B1 | 5/2002 | Whayne et al. |
| 6,391,024 B1 | 5/2002 | Sun et al. |
| 6,428,536 B2 | 8/2002 | Panescu et al. |
| 6,456,864 B1 | 9/2002 | Swanson et al. |
| 6,456,867 B2 | 9/2002 | Reisfeld |
| 6,471,699 B1 | 10/2002 | Fleischman et al. |
| 6,487,441 B1 | 11/2002 | Swanson et al. |
| 6,488,679 B1 | 12/2002 | Swanson et al. |
| 6,490,468 B2 | 12/2002 | Panescu et al. |
| 6,494,880 B1 | 12/2002 | Swanson et al. |
| 6,500,172 B1 | 12/2002 | Panescu et al. |
| 6,508,765 B2 | 1/2003 | Suorsa et al. |
| 6,516,807 B1 | 2/2003 | Panescu et al. |
| 6,522,913 B2 | 2/2003 | Swanson et al. |
| 6,542,773 B2 | 4/2003 | Dupree et al. |
| 6,556,695 B1 | 4/2003 | Packer et al. |
| 6,565,511 B2 | 5/2003 | Panescu et al. |
| 6,569,160 B1 | 5/2003 | Goldin et al. |
| 6,597,955 B2 | 7/2003 | Panescu et al. |
| 6,615,073 B1 | 9/2003 | Panescu et al. |
| 6,625,482 B1 | 9/2003 | Panescu et al. |
| 6,647,281 B2 | 11/2003 | Morency |

(56) References Cited

U.S. PATENT DOCUMENTS

| | | |
|---|---|---|
| 6,652,513 B2 | 11/2003 | Panescu et al. |
| 6,658,279 B2 | 12/2003 | Swanson et al. |
| 6,668,198 B2 | 12/2003 | Swanson et al. |
| 6,735,465 B2 | 5/2004 | Panescu |
| 6,736,811 B2 | 5/2004 | Panescu et al. |
| 6,745,076 B2 | 6/2004 | Wohlgemuth et al. |
| 6,746,401 B2 | 6/2004 | Panescu |
| 6,788,969 B2 | 9/2004 | Dupree et al. |
| 6,790,206 B2 | 9/2004 | Panescu |
| 6,824,515 B2 | 11/2004 | Suorsa et al. |
| 6,895,267 B2 | 5/2005 | Panescu et al. |
| 7,194,294 B2 | 3/2007 | Panescu et al. |
| 7,364,546 B2 | 4/2008 | Panescu et al. |
| 7,505,810 B2 | 3/2009 | Harlev et al. |
| 7,515,954 B2 | 4/2009 | Harlev et al. |
| 7,565,208 B2 | 7/2009 | Harris et al. |
| 7,582,074 B2 | 9/2009 | Rosenfeld et al. |
| 7,582,084 B2 | 9/2009 | Swanson et al. |
| 7,676,264 B1 | 3/2010 | Pillai et al. |
| 7,699,829 B2 | 4/2010 | Harris et al. |
| 7,729,752 B2 | 6/2010 | Harlev et al. |
| 7,774,051 B2 | 8/2010 | Voth |
| 7,794,404 B1 | 9/2010 | Gutfinger et al. |
| 7,869,854 B2 | 1/2011 | Shachar et al. |
| 7,925,349 B1 | 4/2011 | Wong et al. |
| 7,930,018 B2 | 4/2011 | Harlev et al. |
| 7,937,136 B2 | 5/2011 | Harlev et al. |
| 7,945,326 B1 | 5/2011 | Wong et al. |
| 7,946,995 B1 | 5/2011 | Koh et al. |
| 7,953,475 B2 | 5/2011 | Harlev et al. |
| 7,957,791 B2 | 6/2011 | Harlev et al. |
| 7,957,792 B2 | 6/2011 | Harlev et al. |
| 7,957,813 B1 | 6/2011 | Persson et al. |
| 8,010,196 B1 | 8/2011 | Wong et al. |
| 8,019,419 B1 | 9/2011 | Panescu et al. |
| 8,032,218 B2 | 10/2011 | Wong et al. |
| 8,038,625 B2 | 10/2011 | Afonso et al. |
| 8,065,005 B1 | 11/2011 | Wong et al. |
| 8,103,327 B2 | 1/2012 | Harlev et al. |
| 8,103,338 B2 | 1/2012 | Harlev et al. |
| 8,128,617 B2 | 3/2012 | Bencini et al. |
| 8,137,343 B2 | 3/2012 | Harlev et al. |
| 8,165,666 B1 | 4/2012 | Briggs et al. |
| 8,167,876 B2 | 5/2012 | Harlev et al. |
| 8,175,680 B2 | 5/2012 | Panescu |
| 8,202,224 B2 | 6/2012 | Gutfinger et al. |
| 8,208,999 B2 | 6/2012 | Wenzel et al. |
| 8,280,511 B2 | 10/2012 | Zhao et al. |
| 8,306,623 B2 | 11/2012 | Wong et al. |
| 8,364,253 B2 | 1/2013 | Voth |
| 8,369,922 B2 | 2/2013 | Paul et al. |
| 8,386,049 B2 | 2/2013 | Persson et al. |
| 8,406,866 B2 | 3/2013 | Deno et al. |
| 8,414,579 B2 | 4/2013 | Kim et al. |
| 8,449,535 B2 | 5/2013 | Deno et al. |
| 8,504,152 B2 | 8/2013 | Wenzel et al. |
| 8,504,153 B2 | 8/2013 | Wenzel et al. |
| 8,554,333 B2 | 10/2013 | Wu et al. |
| 8,571,647 B2 | 10/2013 | Harlev et al. |
| 8,600,497 B1 | 12/2013 | Yang et al. |
| 8,712,519 B1 | 4/2014 | Panescu et al. |
| 8,830,235 B1 | 9/2014 | Guskov et al. |
| 2001/0000791 A1 | 5/2001 | Suorsa et al. |
| 2001/0009976 A1 | 7/2001 | Panescu et al. |
| 2001/0018608 A1 | 8/2001 | Panescu et al. |
| 2001/0020126 A1 | 9/2001 | Swanson et al. |
| 2001/0025175 A1 | 9/2001 | Panescu et al. |
| 2001/0044585 A1 | 11/2001 | Dupree et al. |
| 2002/0058870 A1 | 5/2002 | Panescu et al. |
| 2002/0065465 A1 | 5/2002 | Panescu et al. |
| 2002/0099415 A1 | 7/2002 | Panescu et al. |
| 2002/0111548 A1 | 8/2002 | Swanson et al. |
| 2002/0115941 A1 | 8/2002 | Whayne et al. |
| 2002/0143250 A1 | 10/2002 | Panescu et al. |
| 2002/0161422 A1 | 10/2002 | Swanson et al. |
| 2002/0193790 A1 | 12/2002 | Fleischman et al. |
| 2002/0198520 A1 | 12/2002 | Coen et al. |
| 2003/0028118 A1 | 2/2003 | Dupree et al. |
| 2003/0055419 A1 | 3/2003 | Panescu et al. |
| 2003/0065322 A1 | 4/2003 | Panescu et al. |
| 2003/0078494 A1 | 4/2003 | Panescu et al. |
| 2003/0078509 A1 | 4/2003 | Panescu |
| 2003/0088244 A1 | 5/2003 | Swanson et al. |
| 2003/0093067 A1 | 5/2003 | Panescu |
| 2003/0093069 A1 | 5/2003 | Panescu et al. |
| 2003/0144655 A1 | 7/2003 | Panescu |
| 2003/0153907 A1 | 8/2003 | Suorsa et al. |
| 2003/0158477 A1 | 8/2003 | Panescu |
| 2003/0199863 A1 | 10/2003 | Swanson et al. |
| 2003/0208123 A1 | 11/2003 | Panescu |
| 2004/0015065 A1 | 1/2004 | Panescu et al. |
| 2004/0097803 A1 | 5/2004 | Panescu |
| 2004/0254437 A1 | 12/2004 | Hauck et al. |
| 2005/0177151 A1 | 8/2005 | Coen et al. |
| 2005/0197657 A1 | 9/2005 | Goth et al. |
| 2005/0215945 A1 | 9/2005 | Harris et al. |
| 2005/0245949 A1 | 11/2005 | Goth et al. |
| 2006/0030833 A1 | 2/2006 | Harris et al. |
| 2006/0064083 A1 | 3/2006 | Khalaj et al. |
| 2006/0089688 A1 | 4/2006 | Panescu |
| 2006/0135957 A1 | 6/2006 | Panescu |
| 2006/0184166 A1 | 8/2006 | Valle et al. |
| 2007/0055227 A1 | 3/2007 | Khalaj et al. |
| 2007/0073179 A1 | 3/2007 | Afonso et al. |
| 2007/0073286 A1 | 3/2007 | Panescu et al. |
| 2007/0156048 A1 | 7/2007 | Panescu et al. |
| 2007/0232949 A1 | 10/2007 | Saksena |
| 2007/0299351 A1 | 12/2007 | Harlev et al. |
| 2007/0299352 A1 | 12/2007 | Harlev et al. |
| 2007/0299353 A1 | 12/2007 | Harlev et al. |
| 2008/0109041 A1 | 5/2008 | de Voir |
| 2008/0190438 A1 | 8/2008 | Harlev et al. |
| 2008/0249424 A1 | 10/2008 | Harlev et al. |
| 2008/0262361 A1 | 10/2008 | Gutfinger et al. |
| 2009/0018597 A1 | 1/2009 | Wenzel et al. |
| 2009/0171274 A1 | 7/2009 | Harlev et al. |
| 2009/0171345 A1 | 7/2009 | Miller et al. |
| 2009/0177071 A1 | 7/2009 | Harlev et al. |
| 2009/0177072 A1 | 7/2009 | Harlev et al. |
| 2009/0253976 A1 | 10/2009 | Harlev et al. |
| 2009/0262109 A1 | 10/2009 | Markowitz et al. |
| 2009/0281439 A1 | 11/2009 | Harlev et al. |
| 2009/0287267 A1 | 11/2009 | Wenzel et al. |
| 2009/0299211 A1 | 12/2009 | Wenzel et al. |
| 2010/0004712 A1 | 1/2010 | Zhao et al. |
| 2010/0023085 A1 | 1/2010 | Wu et al. |
| 2010/0030294 A1 | 2/2010 | Wong et al. |
| 2010/0091834 A1 | 4/2010 | Cheung et al. |
| 2010/0094274 A1 | 4/2010 | Narayan et al. |
| 2010/0106009 A1 | 4/2010 | Harlev et al. |
| 2010/0106154 A1 | 4/2010 | Harlev et al. |
| 2010/0274150 A1 | 10/2010 | Harlev et al. |
| 2010/0286550 A1 | 11/2010 | Harlev et al. |
| 2010/0286551 A1 | 11/2010 | Harlev et al. |
| 2010/0305433 A1 | 12/2010 | Harlev et al. |
| 2010/0324414 A1 | 12/2010 | Harlev et al. |
| 2011/0028821 A1 | 2/2011 | Bojovic et al. |
| 2011/0105928 A1 | 5/2011 | Bojovic et al. |
| 2011/0112413 A1 | 5/2011 | Panescu et al. |
| 2011/0112414 A1 | 5/2011 | Panescu et al. |
| 2011/0112415 A1 | 5/2011 | Bojovic et al. |
| 2011/0125150 A1 | 5/2011 | Deno et al. |
| 2011/0160574 A1 | 6/2011 | Harlev et al. |
| 2011/0166472 A1 | 7/2011 | Björling et al. |
| 2011/0184300 A1 | 7/2011 | Shvilkin et al. |
| 2011/0190625 A1 | 8/2011 | Harlev et al. |
| 2011/0202113 A1 | 8/2011 | Persson et al. |
| 2011/0275949 A1 | 11/2011 | Harlev et al. |
| 2011/0282186 A1 | 11/2011 | Harlev et al. |
| 2011/0282187 A1 | 11/2011 | Harlev et al. |
| 2011/0306896 A1 | 12/2011 | Altmann |
| 2012/0004533 A1 | 1/2012 | Peng et al. |
| 2012/0053470 A1 | 3/2012 | Wong et al. |
| 2012/0078077 A1 | 3/2012 | Harlev et al. |

(56) References Cited

U.S. PATENT DOCUMENTS

| | | |
|---|---|---|
| 2012/0130267 A1 | 5/2012 | Harlev et al. |
| 2012/0143030 A1 | 6/2012 | Harlev et al. |
| 2012/0151301 A1 | 6/2012 | Izumi et al. |
| 2012/0184858 A1 | 7/2012 | Harlev et al. |
| 2012/0184863 A1 | 7/2012 | Harlev et al. |
| 2012/0184864 A1 | 7/2012 | Harlev et al. |
| 2012/0184865 A1 | 7/2012 | Harlev et al. |
| 2012/0245481 A1 | 9/2012 | Blanco et al. |
| 2012/0253161 A1 | 10/2012 | Harlev et al. |
| 2012/0265054 A1 | 10/2012 | Olson |
| 2012/0277574 A1 | 11/2012 | Panescu |
| 2012/0283587 A1 | 11/2012 | Gosh et al. |
| 2013/0035576 A1 | 2/2013 | O'Grady et al. |
| 2013/0060245 A1 | 3/2013 | Grunewald et al. |
| 2013/0096447 A1 | 4/2013 | Dhawan et al. |
| 2013/0123775 A1 | 5/2013 | Grunewald et al. |
| 2013/0137999 A1 | 5/2013 | Wenzel et al. |
| 2013/0138003 A1 | 5/2013 | Kaski |
| 2013/0173222 A1 | 7/2013 | Voth |
| 2013/0204124 A1 | 8/2013 | Duindam et al. |
| 2013/0226016 A1 | 8/2013 | Narayan et al. |
| 2013/0274582 A1 | 10/2013 | Afonso et al. |
| 2013/0303892 A1 | 11/2013 | Zhao et al. |
| 2013/0303945 A1 | 11/2013 | Blumenkranz et al. |
| 2014/0058282 A1* | 2/2014 | O'Grady ............ A61B 5/04884 600/546 |
| 2014/0100440 A1 | 4/2014 | Cheline et al. |
| 2014/0278321 A1 | 9/2014 | Zhang et al. |
| 2014/0310016 A1 | 10/2014 | Kenney et al. |
| 2015/0016749 A1 | 1/2015 | Chen et al. |
| 2015/0065836 A1 | 3/2015 | Thakur et al. |
| 2015/0196215 A1 | 7/2015 | Laughner et al. |
| 2015/0196216 A1 | 7/2015 | Laughner et al. |
| 2015/0250399 A1 | 9/2015 | Laughner et al. |
| 2015/0257671 A1 | 9/2015 | Laughner et al. |

FOREIGN PATENT DOCUMENTS

| | | |
|---|---|---|
| JP | H10137207 A | 5/1998 |
| JP | 200161789 A | 3/2001 |
| JP | 2007536050 A | 12/2007 |
| JP | 2009225976 A | 10/2009 |
| JP | 2011516238 A | 5/2011 |
| JP | 2013523345 A | 6/2013 |
| JP | 2013188439 A | 9/2013 |
| JP | 2014502556 A | 2/2014 |
| WO | 2007029485 A1 | 3/2007 |
| WO | 2007035306 A3 | 3/2007 |
| WO | 2007137045 A2 | 11/2007 |
| WO | 2007146864 A3 | 12/2007 |
| WO | 2008097767 A2 | 8/2008 |
| WO | 2009085108 A1 | 7/2009 |
| WO | 2009123819 A3 | 10/2009 |
| WO | 2010051183 A1 | 5/2010 |
| WO | 2010058372 A1 | 5/2010 |
| WO | 2010123637 A2 | 10/2010 |
| WO | 2010129095 A2 | 11/2010 |
| WO | 2011021948 A1 | 2/2011 |
| WO | 2011142931 A1 | 11/2011 |
| WO | 2011142932 A1 | 11/2011 |
| WO | 2012092016 A1 | 7/2012 |
| WO | 2012097059 A1 | 7/2012 |
| WO | 2012097067 A1 | 7/2012 |
| WO | 2012151301 A1 | 11/2012 |
| WO | 2015066322 A1 | 5/2015 |
| WO | 2015106196 A1 | 7/2015 |
| WO | 2015106201 A1 | 7/2015 |
| WO | 2015106254 A1 | 7/2015 |
| WO | 2015134276 A1 | 9/2015 |

OTHER PUBLICATIONS

International Search Report and Written Opinion issued in PCT/US2014/063148, dated Feb. 4, 2015, 11 pages.
International Search Report and Written Opinion issued in PCT/US2015/011013, dated Sep. 4, 2015, 11 pages.
International Search Report and Written Opinion issued in PCT/US2015/011025, dated Apr. 2, 2015, 8 pages.
International Search Report and Written Opinion issued in PCT/US2015/011170, dated Apr. 28, 2015, 9 pages.
International Search Report and Written Opinion issued in PCT/US2015/017775, dated May 26, 2015, 11 pages.
International Search Report and Written Opinion issued in PCT/US2015/018016, dated May 20, 2015, 13 pages.
Martis, R. J., et. al. A Two-Stage Mechanism for Registration and Classification of ECG Using Gaussian Mixture Model. Pattern Recognition, 42(11): 2979-2988, 2009.
Yilmaz, B., et. al. Usage of Spline Interpolation in Catheter-Based Cardiac Mapping. Turk. J. Elec. Eng. & Comp. Sci., 18(6):989-1002, 2010.
International Preliminary Report on Patentability issued in PCT/US2015/017775 dated Sep. 22, 2016, 7 pages.
International Preliminary Report on Patentability issued in PCT/US2015/018016, dated Sep. 22, 2016, 9 pages.
International Preliminary Report on Patentability issued in PCT/US2015/011013 dated Jul. 28, 2016, 8 pages.
International Preliminary Report on Patentability issued in PCT/US2015/011025, dated Jul. 28, 2016, 6 pages.
International Preliminary Report on Patentability issued in PCT/US2015/011170 dated Jul. 28, 2016, 7 pages.
International Preliminary Report on Patentability issued in PCT/US2014/063148, dated May 12, 2016, 9 pages.
Blanchard, Susan M., et al., "Four Algorithms for Activation Detection from Unipolar Epicardial Electrograms", IEEE Transactions on Biomedical Engineering, 36(2):256-261, Feb. 1, 1989.
Blanchard, Susan M., et al., "Interpolating Unipolar Epicardial Potentials from Electrodes Separated by Increasing Distances", PACE and Clinical Electrophysiology, 12(12):1938-1955, Dec. 1, 1989.
He, Ye H., et al., "An Interactive Graphical System for Automated Mapping and Display of Cardiac Rhythms", Journal of Electrocardiology, 32(3):225-241, Jul. 1, 1999.
Ni, Quan, et al., "A Novel Interpolation Method for Electric Potential Fields in the Heart during Excitation", Annals of Biomedical Engineering, 26(4):597-607, Jul. 1, 1998.
Etienne M. Aliot, et al. "EHRA/HRS Expert Consensus on Catheter Ablation of Ventricular Arrhythmias," European Society of Cardiology. The European Heart Rhythm Association, 11:771-817, 2009.
Deepak Bhakta, et al. "Principles of Electroanatomic Mapping," Indian Pacing and Electrophysiology Journal. Krannert Institute of Cardiology. Indianapolis, Indiana, 8(1):32-50, 2008.
Corinna B. Brunckorst, et al. "Identification of the Ventricular Tachycardia Isthmus After Infarction by Pace Mapping," Circulation Journal of the American Heart Assoication. Volume Circulation, American Heart Association. Dallas, Texas, 110:652-659, Aug. 2, 2004.
William G. Stevenson, et al. Journal of the American College of Cardiology. Fractionated Endocardial Electrograms Are Associated With Slow Conduction in Humans: Evidence From Pace-Mapping, Los Angeles, California, 13(2):369-376, Feb. 1989.
Ken Okumura, et al. "Pathophysiology and Natural History Ventricular Tachycardia. Demonstration of the Presence of Slow Conduction During Sustained Ventricular Tachycardia in Man: Use of Transient Entrainment of the Tachycardia," Department of Medicine, Case Western Reserve University / University Hospitals of Cleveland, Ohio and the University of Alabama at Birmingham, 75(2):369-378. Feb. 1987.
Shiro Nakahara, et al. "Characterization of the Arrhythmogenic Substrate in Ischemic and Nonisohemic Cardiomyopathy. Implications for Catheter Ablation of Hemodynamically Unstable Ventricular Tachycardia," Journal of the American College of Cardiology. Los Angeles, California, 55(21):2355-2365, May 25, 2010.
Takeshi Tsuchiya, et al. "Significance of Late Diastolic Potential Preceding Purkinje Potential in Verapamil-Sensitive Idiopathic Left Ventricular Tachycardia," American Heart Association. Japan, pp. 2408-2413, May 11, 1999.

(56) References Cited

OTHER PUBLICATIONS

Hong Cao, et al. "FEM Analysis of Predicting Electrode-Myocardium Contact From RF Cardiac Catheter Ablation System Impedance," IEEE Transactions on Biomedical Engineering. IEEE Engineering in Medicine and Biology Society. Madison, Wisconsin. 49(6):520-526, Jun. 2002.
Stevenson Wg, et al. "Identifying sites for Catheter Ablation of Ventricular Tachycardia," PubMed NCBI. MeSH Terms, Abstract, Jun. 1992.
Jang-Zern Tsai, et al. "Dependence of Apparent Resistance of Four-Electrode Probes on Insertion Depth," IEEE Transactions on Biomedical Engineering. IEEE Engineering in Medicine and Biology Society. Madison, Wisconsin, 47(1):41-48, Jan. 2000.
Minglong Chen, et al. "Non-contact mapping and linear ablation of the left posterior fascicle during sinus rhythm in the treatment of idiopathic left ventricular tachycardia," European Society of Cardiology. vol. 7: pp. 138-144. Elsevier Ltd. China, 2005.
Jang-Zern Tsai, et al. "Error Analysis of Tissue Resistivity Measurement. IEEE Transactions on Biomedical Engineering," IEEE Engineering in Medicine and Biology Society. Madison, Wisconsin, 49(5):484-494, May 2002.
Ji-Qiang Hu, et al. "The Characteristics of Verapamil-sensitive Idiopathic left Ventricular Tachycardia combined with a left accessory pathway and the effect of radiofrequency catheter ablation," Clinical Research Electrophysiology and Ablation. The European Society of Cardiology. Beijing, China. pp. 704-708, Jun. 30, 2011.
Koonlawee Nademanee, et al. "How to perform Electrogram-guided Atrial Fibrillation Ablation," The Pacific Rim Electrophysiology Research Institute. Heart Rhythm Society. Inglewood, California, 3(8):981-984, Aug. 2006.
Feifan Ouyang, et al. "Electroanatomic Substrate of Idiopathic Left Ventricular Tachycardia: Unidirectional Block and Macroreentry Within the Purkinje Network," Circulation Journal of the American Heart Association. American Heart Association. Dallas, Texas. 105(10):462-469, 2002.

Quan Ni, et al. "A Novel Interpolation Method of Electric Potential Fields in the Heart during Excitation," Annals of Biomedical Engineering. Biomedical Engineering Society. Salt Lake City, Utah. vol. 26:597-607, 1998.
Jason Ng, et al. "Understanding and Interpreting Dominant Frequency Analysis of AF Electrograms," J Cardiovasc Electrophysiol. Blackwell. Chicago, Illinois. 18(6):680-685, 2007.
Koonlawee Nademanee, et al. A New Approach for Catheter Ablation of Atrial Fibrillation: Mapping of the Electrophysiologic Substrate. Journal of the American College of Cardiology. Jun. 2, 2004. 43(11):2044-2053. Elsevier Inc. Inglewood, California; and Bangkok, Thailand.
Nademanee K, et al. "Catheter Ablation of Atrial Fibrillation guided by complex Fractionated Atrial Electrogram Mapping of Atrial Fibrillation Substrate," Pacific Rim Eltrophysiology Research Institute. Elsevier Ltd. Los Angeles, California. 55(3):404-408, May 2010.
Chen I-Ching, et al. "Radiofrequency Ablation Therapy in Concealed Left Free Wall Accessory Pathway With Decremental Conduction," The Cardiopulmonary and Critical Care Journal. CHEST. New York City, New York. pp. 107(1):40-45, Jan. 1995.
Prashanthan Sanders, et al. Spectral Analysis Identifies Sites of High-Frequency Activity Maintaining Atrial Fibrillation in Humans. Circulation Journal of the American Heart Association. The American Heart Association, Inc. Dallas, Texas. 112:789-797, Aug. 9, 2005.
William G. Stevenson, et al. "Recording Techniques of Clinical Electrophysiology," J Cardiovasc Electrophysiol. Blackwell. Boston, Massachusetts. 16(9):1017-1022, 2005.
Joseph B. Morton, et al. "Sensitivity and Specificity of Concealed Entrainment for the Identification of Critical Isthmus in the Atrium: Relationship to Rate, Anatomic Location and Antidromic Penetration," Journal of the American College of Cardiology. Elsevier Science Inc. Melbourne, Australia. 39(5):896-906. Mar. 6, 2002.
William G. Stevenson, et al. "Identification of Reentry Circuit Sites During Catheter Mapping and Radiofrequency Ablation of Ventricular Tachycardia Late After Myocardial Infarction," Circulation. American Heart Association. Los Angeles, California. 88(4):1646-1670, Oct. 1993.

\* cited by examiner

CARDIAC MAPPING USING LATENCY INTERPOLATION

CROSS-REFERENCE TO RELATED APPLICATIONS

This application claims priority under 35 U.S.C. § 119 to U.S. Provisional Application Ser. No. 61/899,033, filed Nov. 1, 2013, the entirety of which is incorporated herein by reference.

TECHNICAL FIELD

The present disclosure pertains to medical devices, and methods for manufacturing medical devices. More particularly, the present disclosure pertains to elongated intracorporeal medical devices including a tubular member connected with other structures, and methods for manufacturing and using such devices.

BACKGROUND OF THE INVENTION

A wide variety of intracorporeal medical devices have been developed for medical use, for example, intravascular use. Some of these devices include guidewires, catheters, and the like. These devices are manufactured by any one of a variety of different manufacturing methods and may be used according to any one of a variety of methods. Of the known medical devices and methods, each has certain advantages and disadvantages. There is an ongoing need to provide alternative medical devices as well as alternative methods for manufacturing and using medical devices.

BRIEF SUMMARY

The invention provides design, material, manufacturing method, and use alternatives for medical devices. An example mapping medical device is disclosed. An example mapping medical device may comprise:
a catheter shaft with a plurality of electrodes coupled thereto, wherein the plurality of electrodes includes a first pair of electrodes, a second pair of electrodes, a third pair of electrodes and a fourth pair of electrodes;
a processor, wherein the processor is configured to:
determine a first latency between the first pair of electrodes;
determine a second latency between the second pair of electrodes;
determine a third latency between the third pair of electrodes;
determine a fourth latency between the fourth pair of electrodes; and
determine a target signal by interpolating the first latency, the second latency, the third latency and the fourth latency.

Alternatively or additionally to any of the embodiments above, wherein determining the target signal further includes sensing a change in electrical potential at the first pair of electrodes over a time period.

Alternatively or additionally to any of the embodiments above, wherein determining the target signal further includes sensing a change in electrical potential at the second pair of electrodes over the time period.

Alternatively or additionally to any of the embodiments above, wherein determining the target signal includes calculating a first intermediate signal.

Alternatively or additionally to any of the embodiments above, wherein determining the target signal includes collecting a first set of data corresponding to the change in electrical potential at the first pair of electrodes over the time period, collecting a second set of data corresponding to the change in electrical potential at the second pair of electrodes over the time period, and timeshifting the first set of data and timeshifting the second set of data.

Alternatively or additionally to any of the embodiments above, wherein calculating the first intermediate signal includes calculating a weighted average of the timeshifted first set of data and the timeshifted second set of data.

Alternatively or additionally to any of the embodiments above, wherein determining the target signal further includes sensing a change in electrical potential at the third pair of electrodes over the time period.

Alternatively or additionally to any of the embodiments above, wherein determining the target signal further includes sensing a change in electrical potential at the fourth pair of electrodes over the time period.

Alternatively or additionally to any of the embodiments above, wherein determining the target signal includes calculating a second intermediate signal.

Alternatively or additionally to any of the embodiments above, wherein determining the target signal includes collecting a third set of data corresponding to the change in electrical potential at the third pair of electrodes over the time period, collecting a fourth set of data corresponding to the change in electrical potential at the fourth pair of electrodes over the time period, and timeshifting the third set of data and timeshifting the fourth set of data.

Alternatively or additionally to any of the embodiments above, wherein calculating a second intermediate signal includes calculating a weighted average of the timeshifted third set of data and the timeshifted fourth set of data.

Alternatively or additionally to any of the embodiments above, wherein determining the target signal includes timeshifting the first intermediate signal, timeshifting the second intermediate signal and calculating a weighted average of the first and second intermediate signals.

Alternatively or additionally to any of the embodiments above, wherein the first pair of electrodes is positioned directly adjacent the second pair of electrodes.

Alternatively or additionally to any of the embodiments above, wherein one or more electrodes are positioned between the first and second pairs of electrodes.

Alternatively or additionally to any of the embodiments above, further comprising the step of ablating a location of the target signal.

Alternatively or additionally to any of the embodiments above, wherein the first pair of electrodes includes a first electrode and a second electrode.

Alternatively or additionally to any of the embodiments above, wherein the second pair of electrodes includes a third electrode and a fourth electrode.

Alternatively or additionally to any of the embodiments above, wherein the third pair of electrodes includes a first electrode and a third electrode.

Alternatively or additionally to any of the embodiments above, wherein the fourth pair of electrodes includes a second electrode and a fourth electrode.

An example method for delivering a medical mapping device comprises:
delivering the medical mapping device of any one of the disclosed embodiments into the heart of a patient.

An example method for mapping an anatomical structure may comprise:

determining a first latency between a first and a second electrode on a medical device;

determining a second latency between a third and a fourth electrode on the medical device;

determining a third latency between a first and a third electrode on the medical device;

determining a fourth latency between a second and a fourth electrode on the medical device; and determining a target signal by interpolating the first latency, the second latency, the third latency and the fourth latency.

Alternatively or additionally to any of the embodiments above, wherein determining the target signal further includes sensing a change in electrical potential at the first electrode over a time period.

Alternatively or additionally to any of the embodiments above, wherein determining the target signal further includes sensing a change in electrical potential at the second electrode over the time period.

Alternatively or additionally to any of the embodiments above, wherein determining the target signal includes calculating a first intermediate signal.

Alternatively or additionally to any of the embodiments above, wherein determining the target signal includes collecting a first set of data corresponding to the change in electrical potential at the first electrode over the time period, collecting a second set of data corresponding to the change in electrical potential at the second electrode over the time period, and timeshifting the first set of data and timeshifting the second set of data.

Alternatively or additionally to any of the embodiments above, wherein calculating a first intermediate signal includes calculating a weighted average of the timeshifted first set of data and the timeshifted second set of data.

Alternatively or additionally to any of the embodiments above, wherein determining the target signal further includes sensing a change in electrical potential at the third electrode over the time period.

Alternatively or additionally to any of the embodiments above, wherein determining the target signal further includes sensing a change in electrical potential at the fourth electrode over the time period.

Alternatively or additionally to any of the embodiments above, wherein determining the target signal includes calculating a second intermediate signal.

Alternatively or additionally to any of the embodiments above, wherein determining the target signal includes collecting a third set of data corresponding to the change in electrical potential at the third electrode over the time period, collecting a fourth set of data corresponding to the change in electrical potential at the fourth electrode over the time period, timeshifting the third set of data and timeshifting the fourth set of data.

Alternatively or additionally to any of the embodiments above, wherein calculating a second intermediate signal includes calculating a weighted average of the timeshifted third set of data and the timeshifted fourth set of data.

Alternatively or additionally to any of the embodiments above, wherein determining the target signal includes timeshifting the first intermediate signal, timeshifting the second intermediate signal and calculating a weighted average of the first and second intermediate signals to determine the target signal Alternatively or additionally to any of the embodiments above, wherein the first electrode is positioned directly adjacent the second electrode.

Alternatively or additionally to any of the embodiments above, wherein one or more electrodes are positioned between the first and second electrodes.

Alternatively or additionally to any of the embodiments above, further comprising the step of ablating a location of the target signal.

An example method for mapping an anatomical structure comprises:

providing a mapping medical device, the medical device including a catheter shaft with a plurality of electrodes coupled thereto, wherein the plurality of electrodes includes a first pair of electrodes, a second pair of electrodes, a third pair of electrodes and a fourth pair of electrodes;

determining a first latency between the first pair of electrodes;

determining a second latency between the second pair of electrodes;

determining a third latency between the third pair of electrodes;

determining a fourth latency between the fourth pair of electrodes; and determining a target signal by interpolating the first latency, the second latency, the third latency and the fourth latency.

Alternatively or additionally to any of the embodiments above, wherein determining the target signal further includes sensing a change in electrical potential at the first pair of electrodes over a time period.

Alternatively or additionally to any of the embodiments above, wherein determining the target signal further includes sensing a change in electrical potential at the second pair of electrodes over the time period.

Alternatively or additionally to any of the embodiments above, wherein the medical device includes a processor and wherein determining the target signal includes using the processor to calculate a first intermediate signal.

Alternatively or additionally to any of the embodiments above, wherein the processor collects a first set of data corresponding to the change in electrical potential at the first pair of electrodes over the time period, wherein the processor collects a second set of data corresponding to the change in electrical potential at the second pair of electrodes over the time period, and wherein the processor timeshifts the first set of data and timeshifts the second set of data.

Alternatively or additionally to any of the embodiments above, wherein using the processor to calculate a first intermediate signal includes calculating a weighted average of the timeshifted first set of data and the timeshifted second set of data.

Alternatively or additionally to any of the embodiments above, wherein determining the target signal further includes sensing a change in electrical potential at the third pair of electrodes over the time period.

Alternatively or additionally to any of the embodiments above, wherein determining the target signal further includes sensing a change in electrical potential at the fourth pair of electrodes over the time period.

Alternatively or additionally to any of the embodiments above, wherein determining the target signal includes using the processor to calculate a second intermediate signal.

Alternatively or additionally to any of the embodiments above, wherein the processor collects a third set of data corresponding to the change in electrical potential at the third pair of electrodes over the time period, wherein the processor collects a fourth set of data corresponding to the change in electrical potential at the fourth pair of electrodes over the time period, and wherein the processor timeshifts the third set of data and timeshifts the fourth set of data.

Alternatively or additionally to any of the embodiments above, wherein using the processor to calculate a second intermediate signal includes calculating a weighted average of the timeshifted third set of data and the timeshifted fourth set of data.

Alternatively or additionally to any of the embodiments above, wherein the processor timeshifts the first intermediate signal, wherein the processor timeshifts the second intermediate signal and wherein the processor calculates a weighted average of the first and second intermediate signals to determine the target signal Alternatively or additionally to any of the embodiments above, the first pair of electrodes is positioned directly adjacent the second pair of electrodes.

Alternatively or additionally to any of the embodiments above, wherein one or more electrodes are positioned between the first and second pairs of electrodes.

Alternatively or additionally to any of the embodiments above, further comprising the step of ablating a location of the target signal.

Alternatively or additionally to any of the embodiments above, wherein the first pair of electrodes includes a first electrode and a second electrode.

Alternatively or additionally to any of the embodiments above, wherein the second pair of electrodes includes a third electrode and a fourth electrode.

Alternatively or additionally to any of the embodiments above, wherein the third pair of electrodes includes a first electrode and a third electrode.

Alternatively or additionally to any of the embodiments above, wherein the fourth pair of electrodes includes a second electrode and a fourth electrode.

The above summary of some embodiments is not intended to describe each disclosed embodiment or every implementation of the present disclosure. The Figures, and Detailed Description, which follow, more particularly exemplify these embodiments.

BRIEF DESCRIPTION OF THE DRAWINGS

The disclosure may be more completely understood in consideration of the following detailed description in connection with the accompanying drawings, in which.

Figure 1:
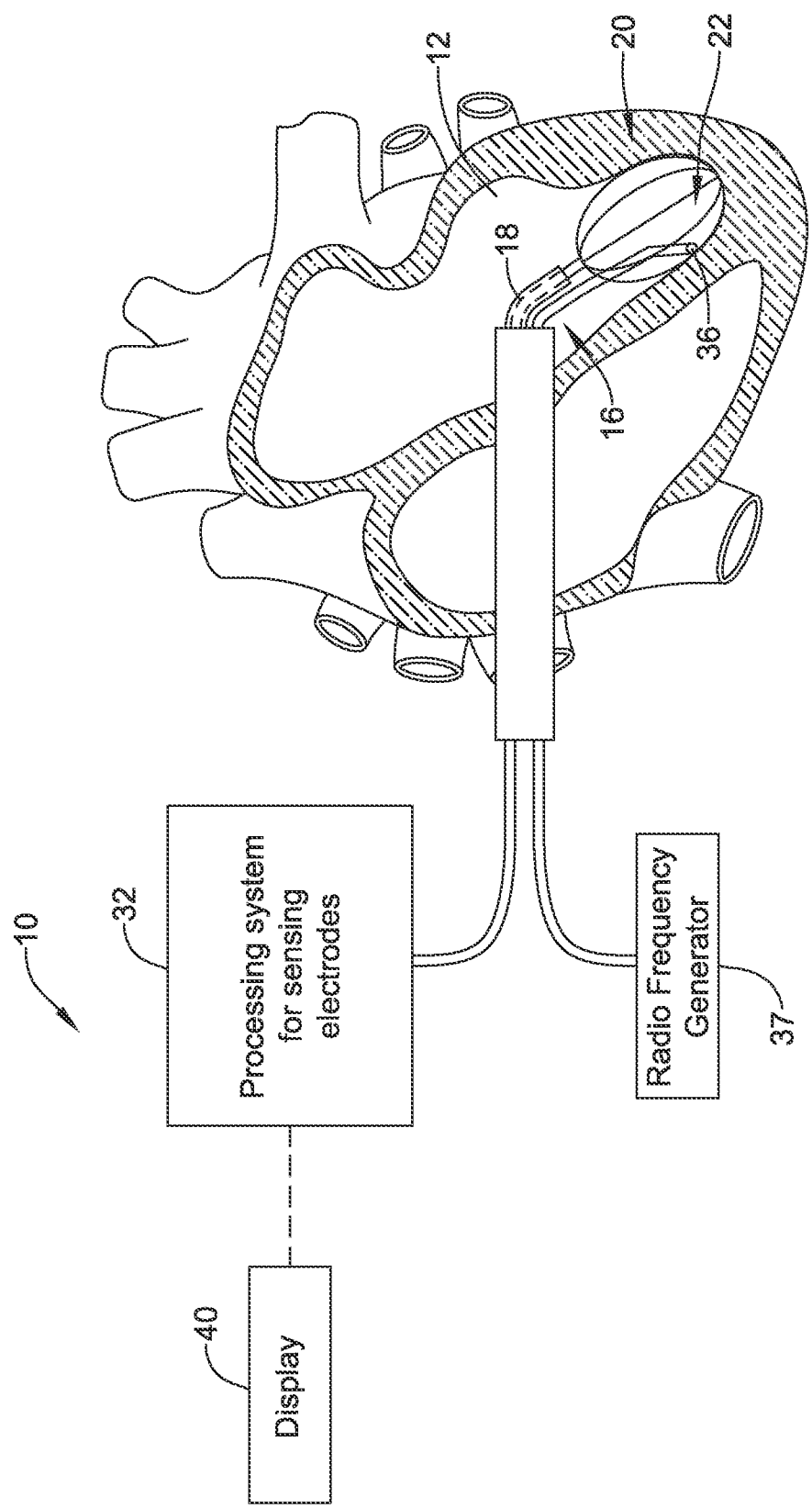
FIG. 1 is a schematic view of an embodiment of a catheter system for accessing a targeted tissue region in the body for diagnostic and therapeutic purposes.

While the disclosure is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include one or more particular features, structures, and/or characteristics. However, such recitations do not necessarily mean that all embodiments include the particular features, structures, and/or characteristics. Additionally, when particular features, structures, and/or characteristics are described in connection with one embodiment, it should be understood that such features, structures, and/or characteristics may also be used connection with other embodiments whether or not explicitly described unless clearly stated to the contrary.

The following detailed description should be read with reference to the drawings in which similar elements in different drawings are numbered the same. The drawings, which are not necessarily to scale, depict illustrative embodiments and are not intended to limit the scope of the invention.

Mapping the electrophysiology of heart rhythm disorders often involves the introduction of a constellation catheter or other mapping/sensing device having a plurality of sensors into a cardiac chamber. The sensors detect the electric activity of the heart at sensor locations. It may be desirable to have the electric activity processed into electrogram signals that accurately represent cellular excitation through cardiac tissue relative to the sensor locations. A processing system may then analyze and output the signal to a display device. The physician may use the displayed information to perform a diagnostic procedure. However, in some cases the sensing electrodes may fail to accurately detect electrical activity of heart. For example, the sensors may fail entirely to detect a signal or they may detect far-field electrical activity and/or electrical artifacts.

The processing system may be configured to detect a variety of activation signals generated by the electrical activity of the myocardial tissue and sensed by adjacent electrodes. However, a limited number of electrodes on the constellation catheter or other mapping/sensing device may limit the resolution of the activation pattern sensing. Therefore, it may be desirable to interpolate a weak or non-existent activation signal. Standard interpolation methods may have limitations due to the transient nature of activation signals and the non-instantaneous nature of activation signal propagation across electrodes. The methods and systems disclosed herein are designed to overcome at least some of the limitations of standard interpolation methods to interpolate weak or non-existent activation signals. For example, some of the methods disclosed herein may include interpolating methods that account for latency effects inherent in the propagation of cellular excitation signals. Other methods and medical devices are also disclosed.

FIG. 1 is a schematic view of a system 10 for accessing a targeted tissue region in the body for diagnostic and/or therapeutic purposes. FIG. 1 generally shows the system 10 deployed in the left atrium of the heart. Alternatively, system 10 can be deployed in other regions of the heart, such as the left ventricle, right atrium, or right ventricle. While the illustrated embodiment shows the system 10 being used for ablating myocardial tissue, the system 10 (and the methods described herein) may alternatively be configured for use in other tissue ablation applications, such as procedures for ablating tissue in the prostrate, brain, gall bladder, uterus, nerves, blood vessels and other regions of the body, including in systems that are not necessarily catheter-based.

The system 10 includes a mapping probe 14 and an ablation probe 16. In FIG. 1, each is separately introduced into the selected heart region 12 through a vein or artery (e.g., the femoral vein or artery) through suitable percutaneous access.

Alternatively, the mapping probe 14 and ablation probe 16 can be assembled in an integrated structure for simultaneous introduction and deployment in the heart region 12.

The mapping probe 14 may have a flexible catheter body 18. The distal end of the catheter body 18 carries a three-dimensional multiple electrode structure 20. In the illustrated embodiment, the structure 20 takes the form of a basket defining an open interior space 22 (see FIG. 2), although other multiple electrode structures could be used wherein the geometry of the electrode structure and electrode locations may be known. The multiple electrode structure 20 carries a plurality of mapping electrodes 24 (not explicitly shown on FIG. 1, but shown on FIG. 2) each having an electrode location and channel. Each electrode 24 may be configured to sense intrinsic physiological activity in the anatomical region. In some embodiments, the electrodes 24 may be configured to detect activation signals of the intrinsic physiological activity within the anatomical structure, e.g., the activation times of cardiac activity.

The electrodes 24 are electrically coupled to a processing system 32. A signal wire (not shown) may be electrically coupled to each electrode 24 on the basket structure 20. The wires extend through the body 18 of the probe 14 and electrically couple each electrode 24 to an input of the processing system 32, as will be described later in greater detail. The electrodes 24 sense intrinsic electrical activity in the anatomical region, e.g., myocardial tissue. The sensed activity, e.g. activation signals, is processed by the processing system 32 to assist the physician by generating an anatomical map, e.g., a vector field map, to identify the site or sites within the heart appropriate for a diagnostic and/or treatment procedure, e.g. an ablation procedure. For example, the processing system 32 may identify a near-field signal component, i.e. activation signals originating from cellular tissue adjacent to the mapping electrode 24, or from an obstructive far-field signal component, i.e. activation signals originating from non-adjacent tissue. For example, the near-field signal component may include activation signals originating from atrial myocardial tissue whereas the far-field signal component may include activation signals originating from ventricular myocardial tissue. The near-field activation signal component may be further analyzed to find the presence of a pathology and to determine a location suitable for ablation for treatment of the pathology, e.g., ablation therapy.

The processing system 32 includes dedicated circuitry (e.g., discrete logic elements and one or more microcontrollers; application-specific integrated circuits (ASICs); or specially configured programmable devices, such as, for example, programmable logic devices (PLDs) or field programmable gate arrays (FPGAs)) for receiving and/or processing the acquired activation signals. In some embodiments, the processing system 32 includes a general purpose microprocessor and/or a specialized microprocessor (e.g., a digital signal processor, or DSP, which may be optimized for processing activation signals) that executes instructions to receive, analyze and display information associated with the received activation signals. In such implementations, the processing system 32 can include program instructions, which when executed, perform part of the signal processing. Program instructions can include, for example, firmware, microcode or application code that is executed by microprocessors or microcontrollers. The above-mentioned implementations are merely exemplary, and the reader will appreciate that the processing system 32 can take any suitable form.

In some embodiments, the processing system 32 may be configured to measure the intrinsic electrical activity in the myocardial tissue adjacent to the electrodes 24. For example, in some embodiments, the processing system 32 is configured to detect intrinsic electrical activity associated with a dominant rotor or divergent activation pattern in the anatomical feature being mapped. For example, dominant rotors and/or divergent activation patterns may have a role in the initiation and maintenance of atrial fibrillation, and ablation of the rotor path, rotor core, and/or divergent foci may be effective in terminating the atrial fibrillation. In either situation, the processing system 32 processes the sensed activation signals to generate a display of relevant characteristic, such as an APD map, a vector field map, a contour map, a reliability map, an electrogram, a cardiac action potential and the like. The relevant characteristics may be used by the physician to identify a site suitable for ablation therapy.

The ablation probe 16 includes a flexible catheter body 34 that carries one or more ablation electrodes 36. The one or more ablation electrodes 36 are electrically connected to a radio frequency generator (RF) 37 that is configured to deliver ablation energy to the one or more ablation electrodes 36. The ablation probe 16 may be movable with respect to the anatomical feature to be treated, as well as the structure 20. The ablation probe 16 may be positionable between or adjacent to electrodes 24 of the structure 20 as the one or more ablation electrodes 36 are positioned with respect to the tissue to be treated.

The processing system 32 outputs to a device 40 the display of relevant characteristics for viewing by a physician. In the illustrated embodiment, device 40 is a CRT, LED, or other type of display, or a printer). The device 40 presents the relevant characteristics in a format most useful to the physician. In addition, the processing system 32 may generate position-identifying output for display on the device 40 that aids the physician in guiding the ablation electrode(s) 36 into contact with tissue at the site identified for ablation.

Figure 2:
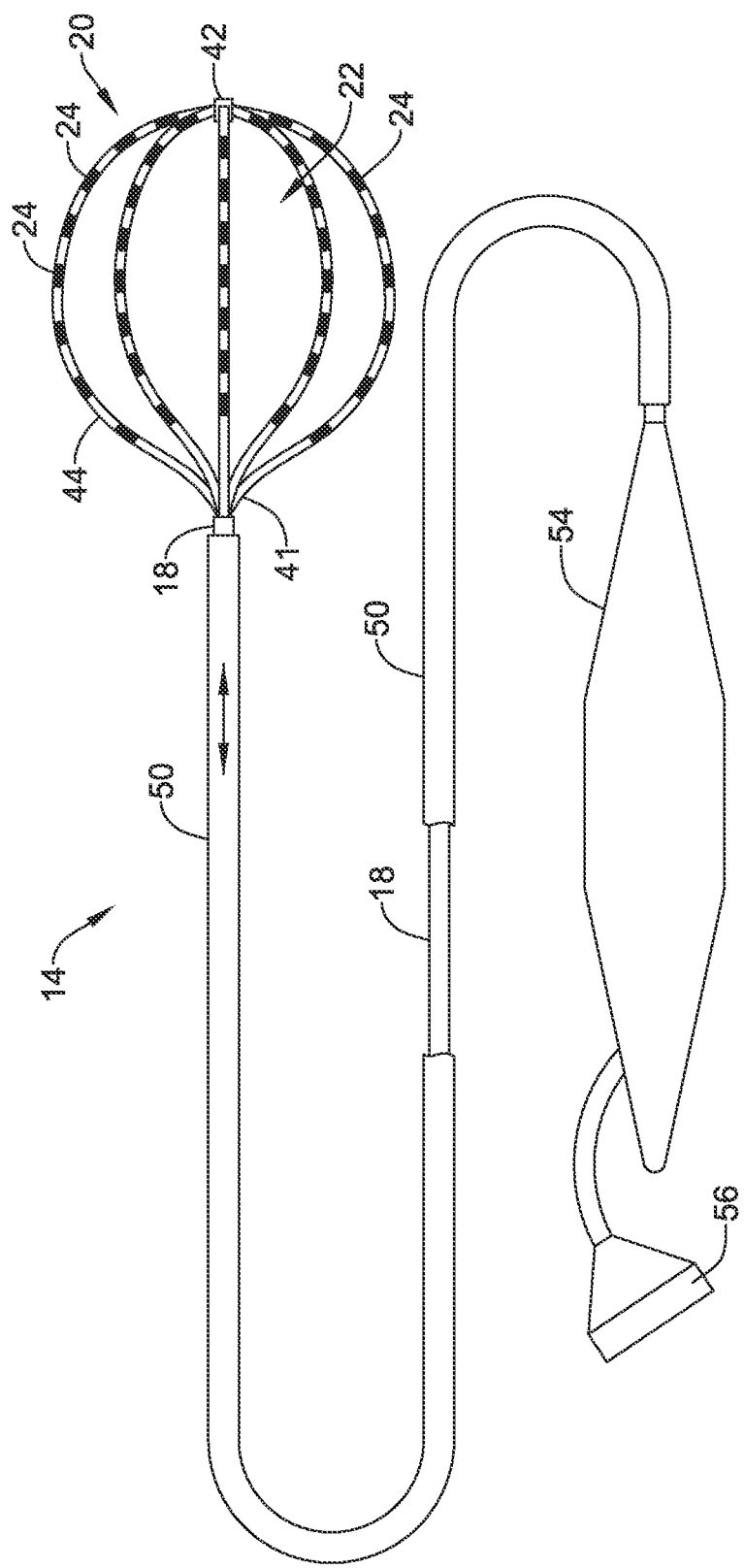
FIG. 2 is a schematic view of an embodiment of a mapping catheter having a basket functional element carrying structure for use in association with the system of FIG. 1.

FIG. 2 illustrates an embodiment of the mapping catheter 14 including electrodes 24 at the distal end suitable for use in the system 10 shown in FIG. 1. The mapping catheter 14 has a flexible catheter body 18, the distal end of which carries the three dimensional structure 20 configured to carry the mapping electrodes or sensors 24. The mapping electrodes 24 sense intrinsic electrical activity, e.g., activation signals, in the myocardial tissue, the sensed activity is then processed by the processing system 32 to assist the physician in identifying the site or sites having a heart rhythm disorder or other myocardial pathology via a generated and displayed relevant characteristics. This information can then be used to determine an appropriate location for applying appropriate therapy, such as ablation, to the identified sites, and to navigate the one or more ablation electrodes 36 to the identified sites.

The illustrated three-dimensional structure 20 comprises a base member 41 and an end cap 42 between which flexible splines 44 generally extend in a circumferentially spaced relationship. As discussed above, the three dimensional structure 20 takes the form of a basket defining an open interior space 22. In some embodiments, the splines 44 are made of a resilient inert material, such as Nitinol metal or silicone rubber, and are connected between the base member 41 and the end cap 42 in a resilient, pretensed condition, to bend and conform to the tissue surface they contact. In the illustrated embodiment, eight splines 44 form the three dimensional structure 20. Additional or fewer splines 44 could be used in other embodiments. As illustrated, each spline 44 carries eight mapping electrodes 24. Additional or fewer mapping electrodes 24 could be disposed on each spline 44 in other embodiments of the three dimensional structure 20. In the illustrated embodiment, the three dimensional structure 20 is relatively small (e.g., 40 mm or less in diameter). In alternative embodiments, the three dimensional structure 20 is even smaller or larger (e.g., 40 mm in diameter or greater).

A slidable sheath 50 may be movable along the major axis of the catheter body 18. Moving the sheath 50 forward (i.e., toward the distal end) causes the sheath 50 to move over the three dimensional structure 20, thereby collapsing the structure 20 into a compact, low profile condition suitable for introduction into and/or removal from an interior space of an anatomical structure, such as, for example, the heart. In contrast, moving the sheath 50 rearward (i.e., toward the proximal end) exposes the three dimensional structure 20, allowing the structure 20 to elastically expand and assume the pretensed position illustrated in FIG. 2.

A signal wire (not shown) is electrically coupled to each mapping electrode 24. The wires extend through the body 18 of the mapping catheter 20 into a handle 54, in which they are coupled to an external connector 56, which may be a multiple pin connector. The connector 56 electrically couples the mapping electrodes 24 to the processing system 32. Further details on mapping systems and methods for processing signals generated by the mapping catheter are discussed in U.S. Pat. No. 6,070,094, entitled "Systems and Methods for Guiding Movable Electrode Elements within Multiple Electrode Structure," U.S. Pat. No. 6,233,491, entitled "Cardiac Mapping and Ablation Systems," and U.S. Pat. No. 6,735,465, entitled "Systems and Processes for Refining a Registered Map of a Body Cavity," the disclosures of which are hereby expressly incorporated herein by reference.

Figure 3:
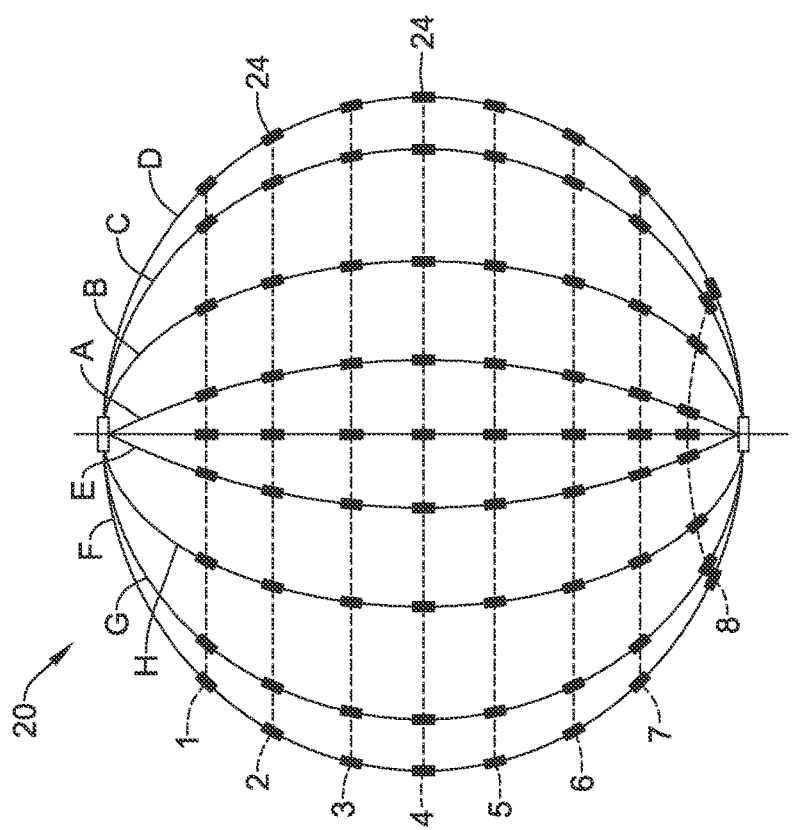
FIG. 3 is a schematic view of an embodiment of the basket functional element including a plurality of mapping electrodes.

To illustrate the operation of the system 10, FIG. 3 is a schematic side view of an embodiment of the basket structure 20 including a plurality of mapping electrodes 24. In the illustrated embodiment, the basket structure includes 64 mapping electrodes 24. The mapping electrodes 24 are disposed in groups of eight electrodes (labeled 1, 2, 3, 4, 5, 6, 7, and 8) on each of eight splines (labeled A, B, C, D, E, F, G, and H). While an arrangement of sixty-four mapping electrodes 24 is shown disposed on a basket structure 20, the mapping electrodes 24 may alternatively be arranged in different numbers, on different structures, and/or in different positions. In addition, multiple basket structures can be deployed in the same or different anatomical structures to simultaneously obtain signals from different anatomical structures.

After the basket structure 20 is positioned adjacent to the anatomical structure to be treated (e.g. left atrium, left ventricle, right atrium, or right ventricle of the heart), the processing system 32 is configured to record the activation signals from each electrode 24 channel related to physiological activity of the anatomical structure, i.e. the electrodes 24 measure electrical activation signals intrinsic to the physiology of the anatomical structure. The activation signals of physiological activity can be sensed in response to intrinsic physiological activity or based on a predetermined pacing protocol instituted by at least one of the plurality of electrodes 24.

Figure 4:
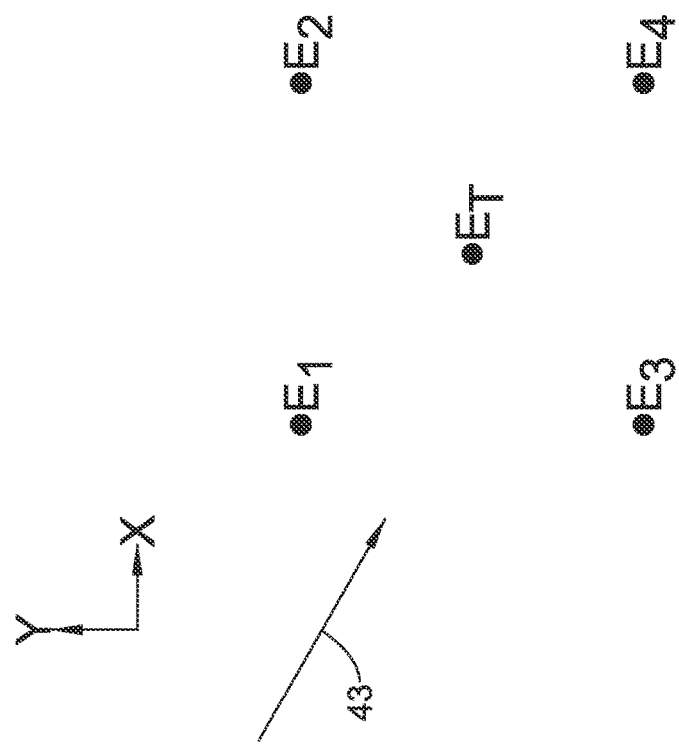
FIG. 4 is an illustration of an example excitation wavefront and four electrodes arranged in a 2×2 distribution.

FIG. 4 illustrates an example cellular activation wavefront propagating in the direction of four electrodes (E1, E2, E3 and E4) arranged in a 2×2 electrode distribution. It is contemplated that this disclosure may also apply to any number of electrode distributions. In this embodiment, the electrode configuration may be representative of four electrodes arranged on a constellation catheter, basket structure or similar sensing device. FIG. 4 generally illustrates the direction of cellular firing by the wavefront vector arrow 43, traveling toward electrodes E1, E2, E3 and E4. In this example, the direction of the wavefront vector 43 shows that the wavefront would likely reach electrode E1 before E2, E3 or E4. As the cells underlying electrode E1 depolarize in response to a change in electrical membrane potential, electrode E1 may "sense" an "activation event," i.e. a change in electrical potential relative to the cells' resting state potential. In response, E1 may collect and send the change in electrical potential data to a processing system 32 which may output an electrogram signal to a display 40. Similarly, if adjacent cells fire in response to a change in electrical potential of adjacent cells, the wavefront may propagate toward electrode E2. Electrode E2 may then sense the change in electrical potential in a similar manner as electrode E1. The time lapse between the sensing of a change in electrical potential of cellular firing of E1 to E2 can be characterized as a latency time interval between the sensing by E1 and E2.

The direction of cellular activation wavefront propagation in a normal heart may occur in preferential directions. However, in a disease state, the myocardial tissue (i.e. cardiac myocytes) may not behave "normally." Rather, cellular firing may occur in multiple directions relative to position of sensing electrodes along a constellation catheter or similar sensing device. For example, the example wavefront vector 43 illustrated in FIG. 4 may represent a path of cellular firing which is not directly aligned in either the X or Y direction relative to electrodes E1, E2, E3 and E4. However, the wavefront vector can be understood to be the summation of a wavefront vector component in the X direction and a wavefront vector component in the Y direction. Therefore, as the activation wavefront approaches electrodes E1-E4, electrode E1 will likely sense the example wavefront first, followed by electrodes E2, E3 and E4 in the order in which the wavefront reaches each of E2-E4, respectively.

It can be appreciated that if a second wavefront approached electrodes E1-E4 from a direction different from that of the first wavefront, electrodes E1-E4 may sense the second wavefront propagation in a different order than the first wavefront, depending on the precise path that the cellular firing occurs relative to the electrode distribution. For example, the wavefront may reach E3, followed by E4, E1 and then E2. Further, it can be appreciated that because each wavefront vector is a summation of vector components in the X and Y directions, latencies may be calculated between the sensing of any of E1, E2, E3 and E4 in any order.

As indicated above, it may be desirable to sense, map and display cellular activation propagation signals generated by the electrical activity of myocardial tissue. For example, it may be desirable to display activation signals correlating to the electrical discharge of myocardial cells. The shape of the signals may indicate abnormal wavefront excitation propagation.

The arrangement, size, spacing and location of electrodes along a constellation catheter or other mapping/sensing device, in combination with the specific geometry of the targeted anatomical structure, may dictate the accuracy with which sensing electrodes collect and transmit electrical activity of targeted cellular tissue. For example, a limited number of electrodes present on a constellation catheter or other sensing device may decrease the resolution of the data acquired from the target activation pattern sensing. Because it may not be practical or desirable to increase the number of electrodes or decrease the spacing between electrodes on the sensing device, it may be desirable to interpolate an electrical signal occurring between electrodes. For example, in addition to sensing cellular firing at electrode locations E1-E4, it may be desirable to approximate cellular firing at some location intermediate electrodes E1-E4.

Figure 5:
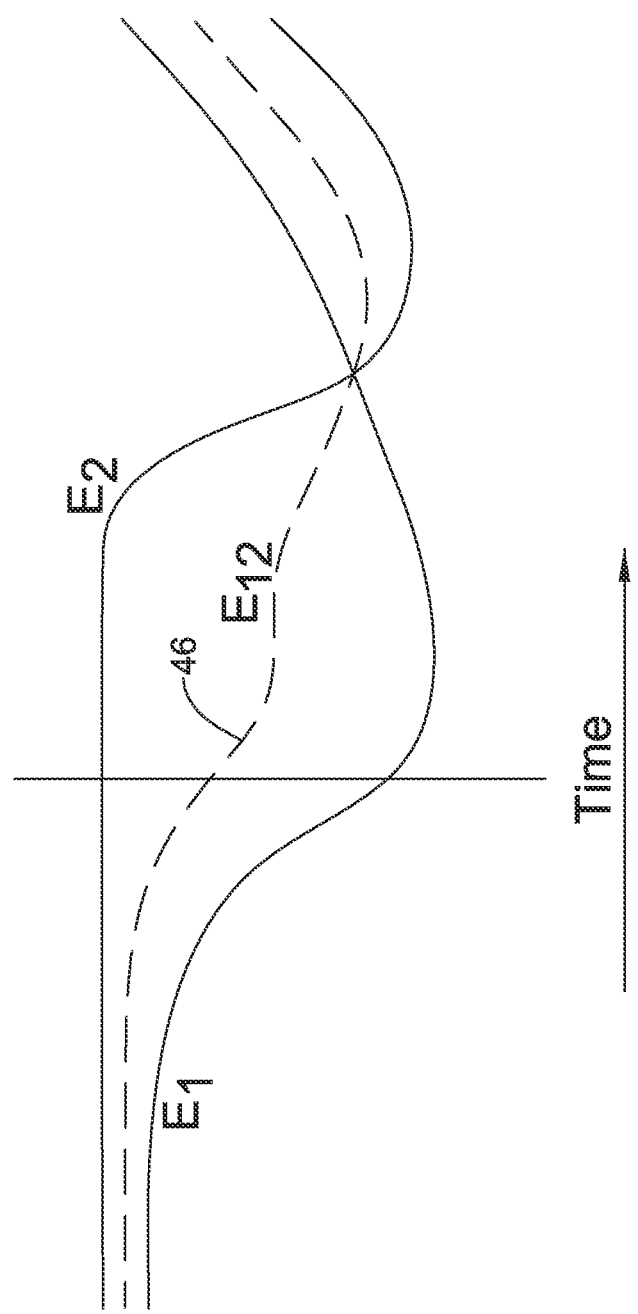
FIG. 5 is an illustration of two example electrogram signals and an example electrogram of a targeted signal.

FIG. 5 illustrates two example electrograms generated from a cellular excitation wavefront passing underneath two example electrodes E1 and E2. In this example, the wavefront passes under E1 at a time before it passes under E2. As shown in the figures, the example electrogram for each electrode sensor visually represents the depolarization of the cells underlying electrodes E1 and E2 at different times. The time delay between the firing of cells underneath E1 and cells underneath E2 may be referred to as the "latency" between E1 and E2. Further, FIG. 5 illustrates an "interpolated" electrogram of a theoretical electrode (labeled $E_{12}$) which would theoretically be located at a point between E1 and E2. Utilizing standard linear interpolation methods, without taking into account the latency present between the cellular firing of E1 and E2, may result in an electrogram represented by the dashed line 46 in FIG. 5. Using standard interpolation methods, therefore, results in an interpolated electrogram whose shape is unrepresentative of the electrograms (i.e. E1 & E2) from which the interpolated electrogram (Eu) is derived. Therefore, an interpolation method which accounts for latency effects may provide a more accurate interpolated electrogram.

Figure 6:
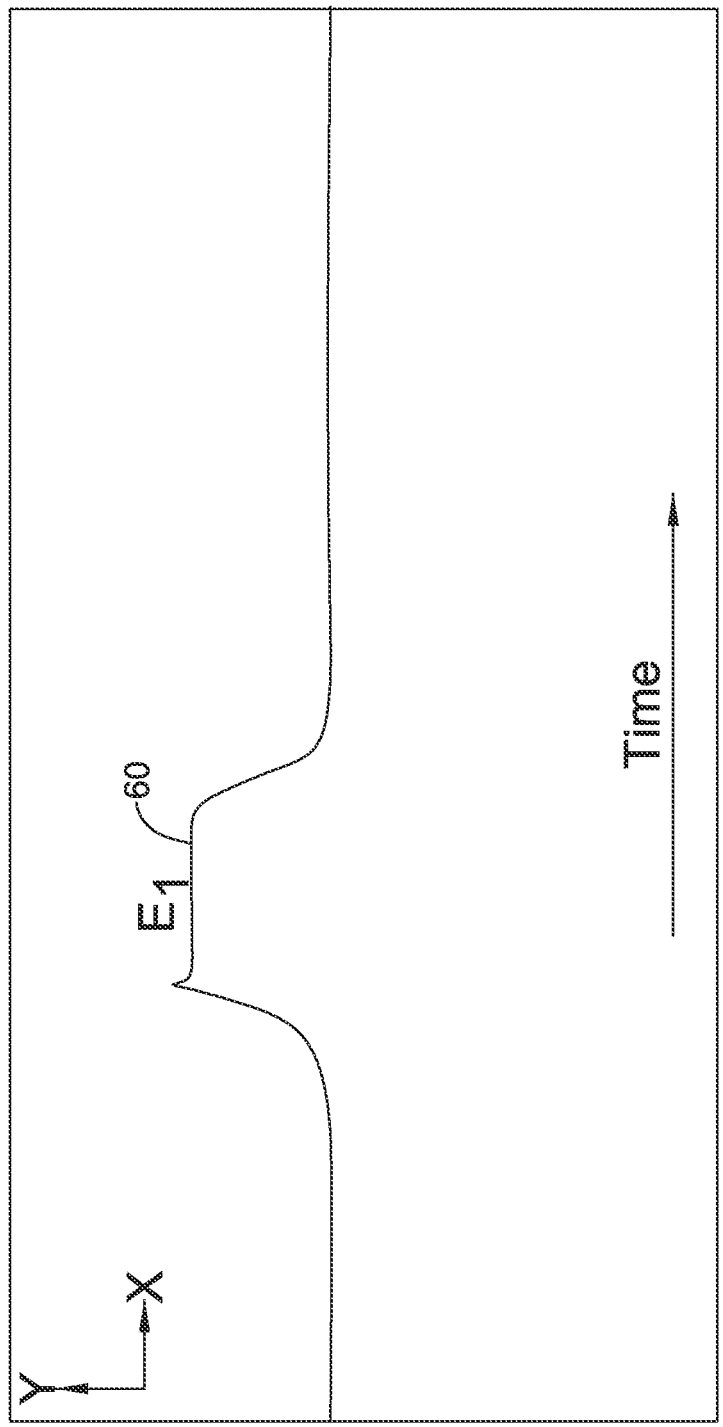
FIG. 6 is an illustration of an example electrogram signal over a time period positioned in a coordinate system.

FIG. 6 illustrates an example electrogram 60 generated from an example electrode E1 located at an example position in a Cartesian coordinate system. While the position of E1 in FIG. 6 is located within X & Y coordinates, it is contemplated that E1 could be located at any position in 3-dimensional space. Electrode E1 may represent an electrode positioned along a spline of a constellation catheter or similar sensing device such as those shown herein. As an example cellular activation wavefront passes underneath E1 over a time period, an electrogram 60 is generated which graphically displays the voltage potential of depolarizing cell relative to their resting voltage.

Figure 7:
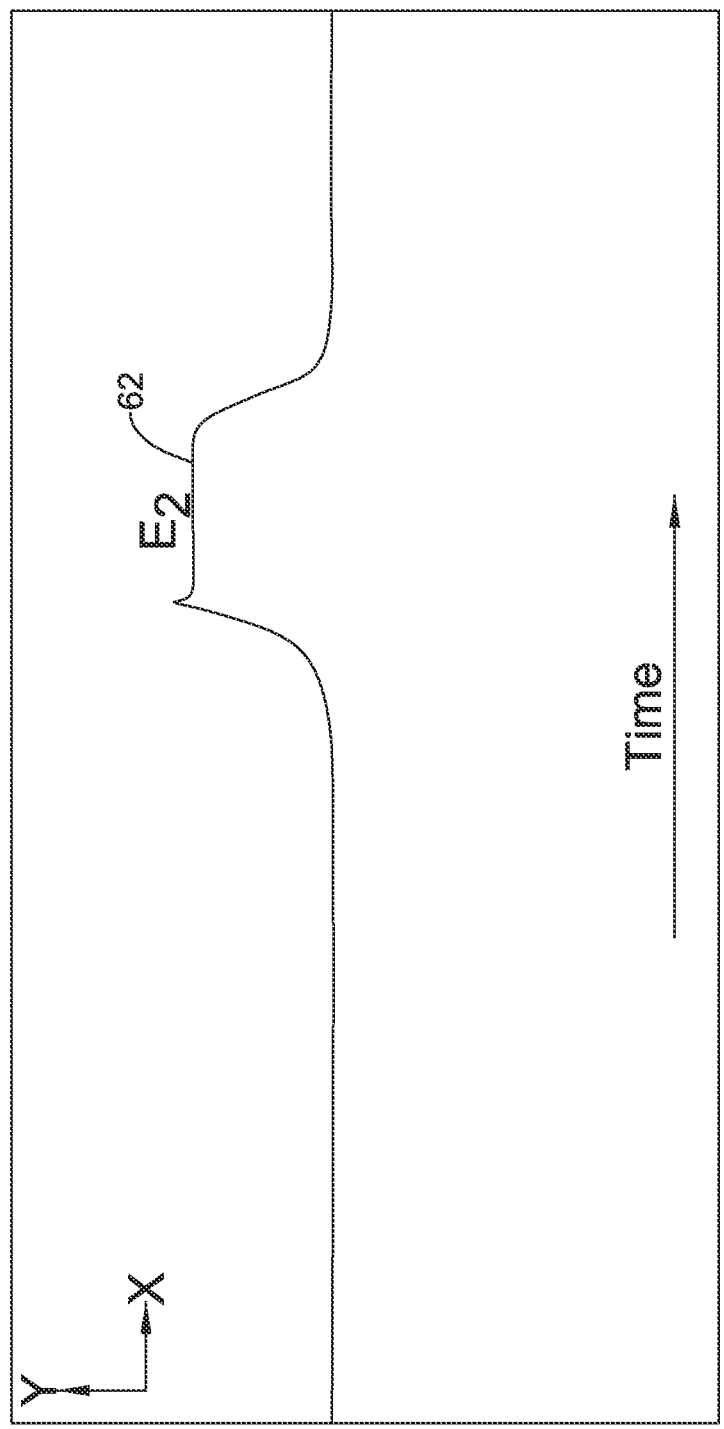
FIG. 7 is an illustration of an example electrogram signal over a time period positioned in a coordinate system.
Figure 8:
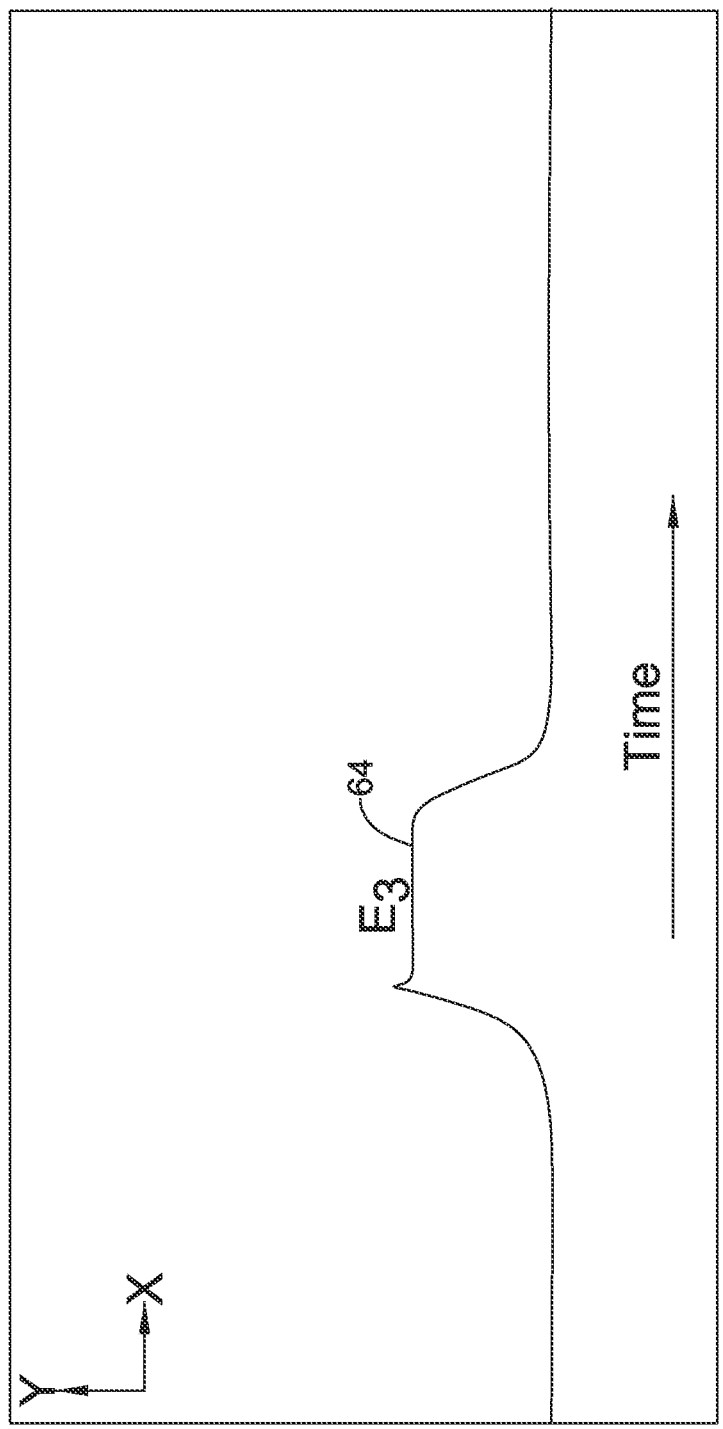
FIG. 8 is an illustration of an example electrogram signal over a time period positioned in a coordinate system.
Figure 9:
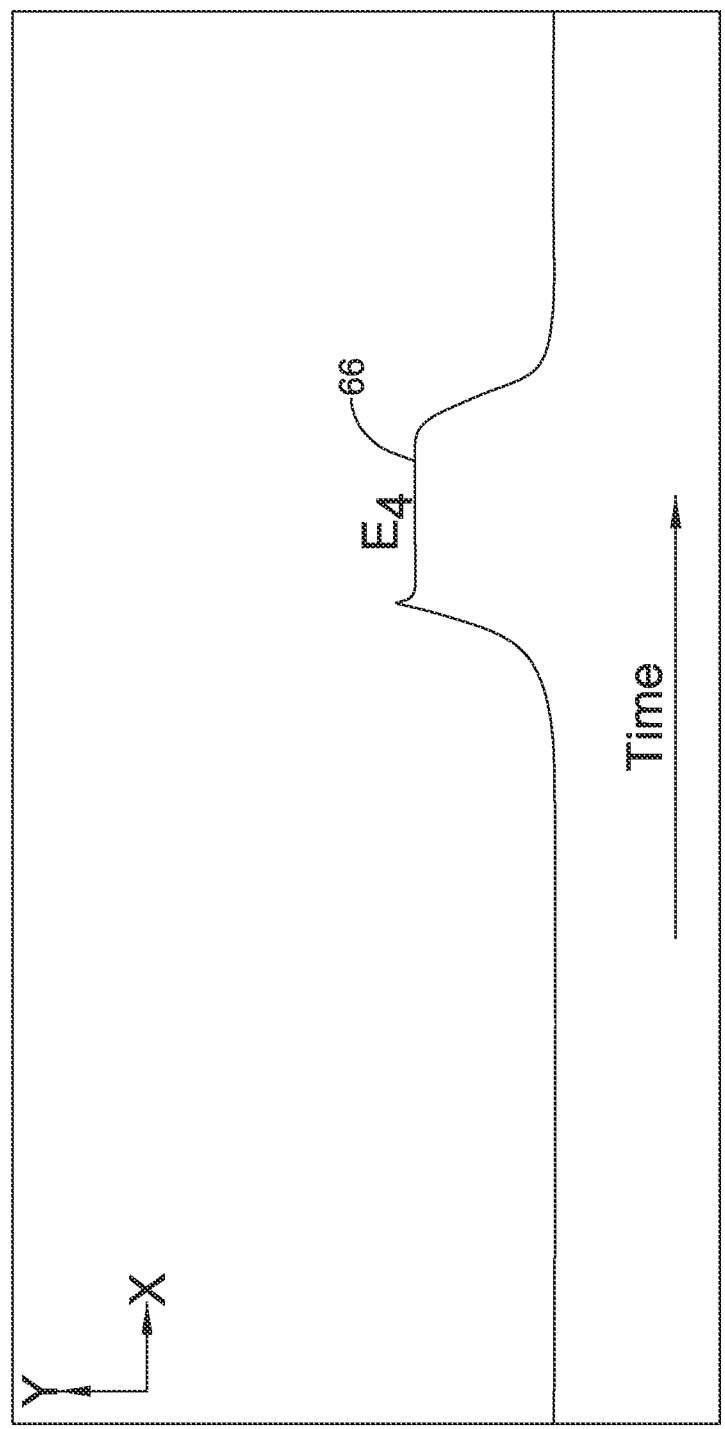
FIG. 9 is an illustration of an example electrogram signal over a time period positioned in a coordinate system.

Similarly, FIGS. 7-9 illustrate example electrograms 62, 64, 66 generated from example electrodes E2, E3 and E4 located at an example position in a Cartesian coordinate system. While the position of E2, E3 and E4 in FIGS. 7-9 are located within X & Y coordinates, it is contemplated that E2, E3 and E4 could be located at any position in 3-dimensional space. Electrodes E2, E3 and E4 may represent electrodes positioned along a spline of a constellation catheter or similar sensing device. As an example cellular activation wavefront passes underneath E2, E3 or E4 over a time period, electrograms 62, 64, 66 are generated which graphically displays the voltage potential of depolarizing cells relative to their resting voltage.

Figure 10:
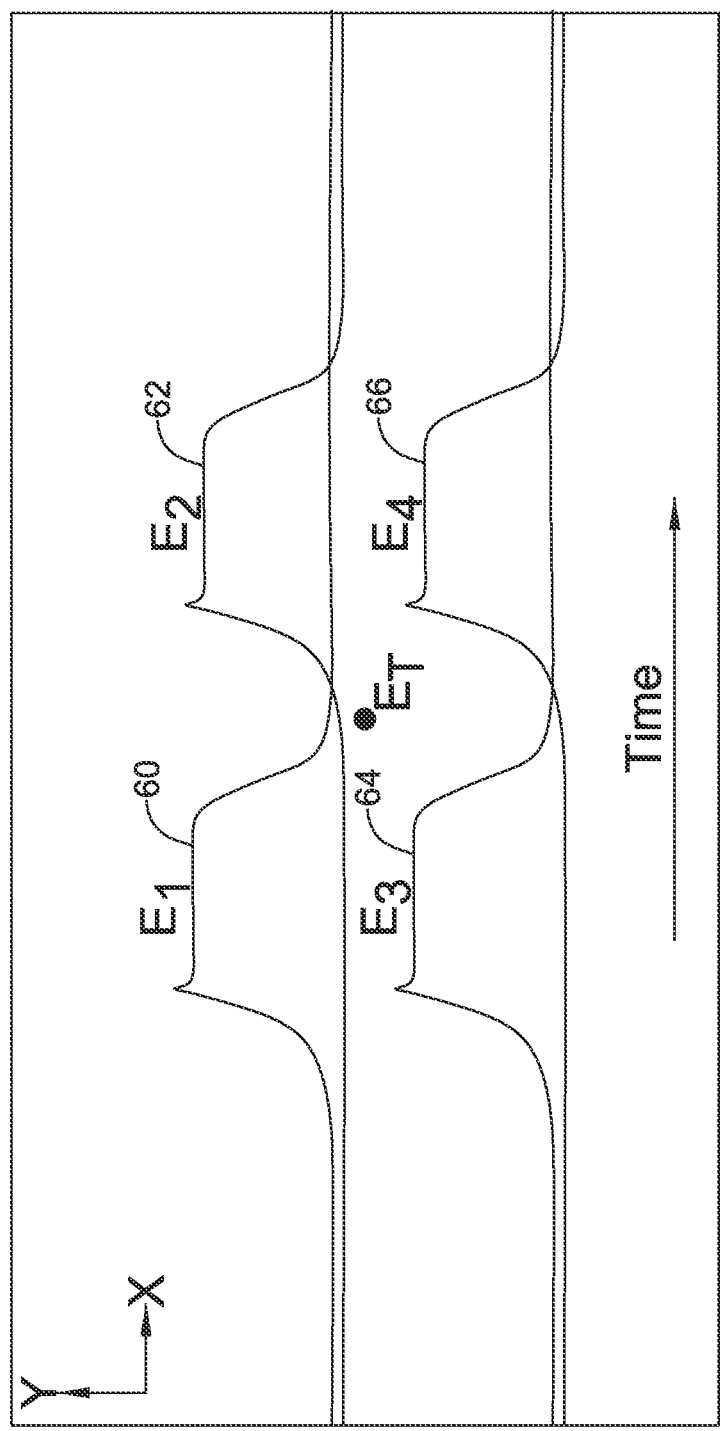
FIG. 10 is an illustration of the example electrogram signals of FIGS. 6-9 positioned in a coordinate system.

FIG. 10 is a schematic example of the collection of electograms 60, 62, 64, 66 of example electrodes E1-E4 described in FIGS. 6-9. As can be seen from FIG. 10, each of electrodes E1-E4 are positioned apart from one another at example positions in a Cartesian coordinate system. Similarly to FIGS. 6-9, while the position of E2, E3 and E4 in FIGS. 7-9 are located within X & Y coordinates, it is contemplated that E2, E3 and E4 could be located at any position in 3-dimensional space. Electrodes E2, E3 and E4 may represent electrodes positioned along a spline of a constellation catheter or similar sensing device. As an example cellular activation wavefront passes underneath E2, E3 or E4 over a time period, the electrograms 60, 62, 64, 66 are generated which graphically display the voltage potential of depolarizing cells relative to their resting voltage. Further, FIG. 10 illustrates the location of an example target electrode (labeled $E_T$). It may be desirable to interpolate the electrogram of target electrode $E_T$ based on the data sensed and collected by electrodes E1-E4.

Accordingly, an example embodiment may include a catheter body 18 including a plurality of electrodes 24 designed to be inserted into a cardiac chamber of a patient's heart. For example, the electrode structure 20 may be a constellation catheter or similar sensing device. As stated above, the plurality of electrodes 24 may be connected to a processor 32. The processor 32 may collect, analyze and output data related to example electrodes E1-E4 discussed above. Further, the processor 32 may analyze and generate an interpolated electrogram of an example targeted electrode $E_T$ discussed above. The processor 32 may output the date relating to the electrogram to a display device 40.

Figure 11:
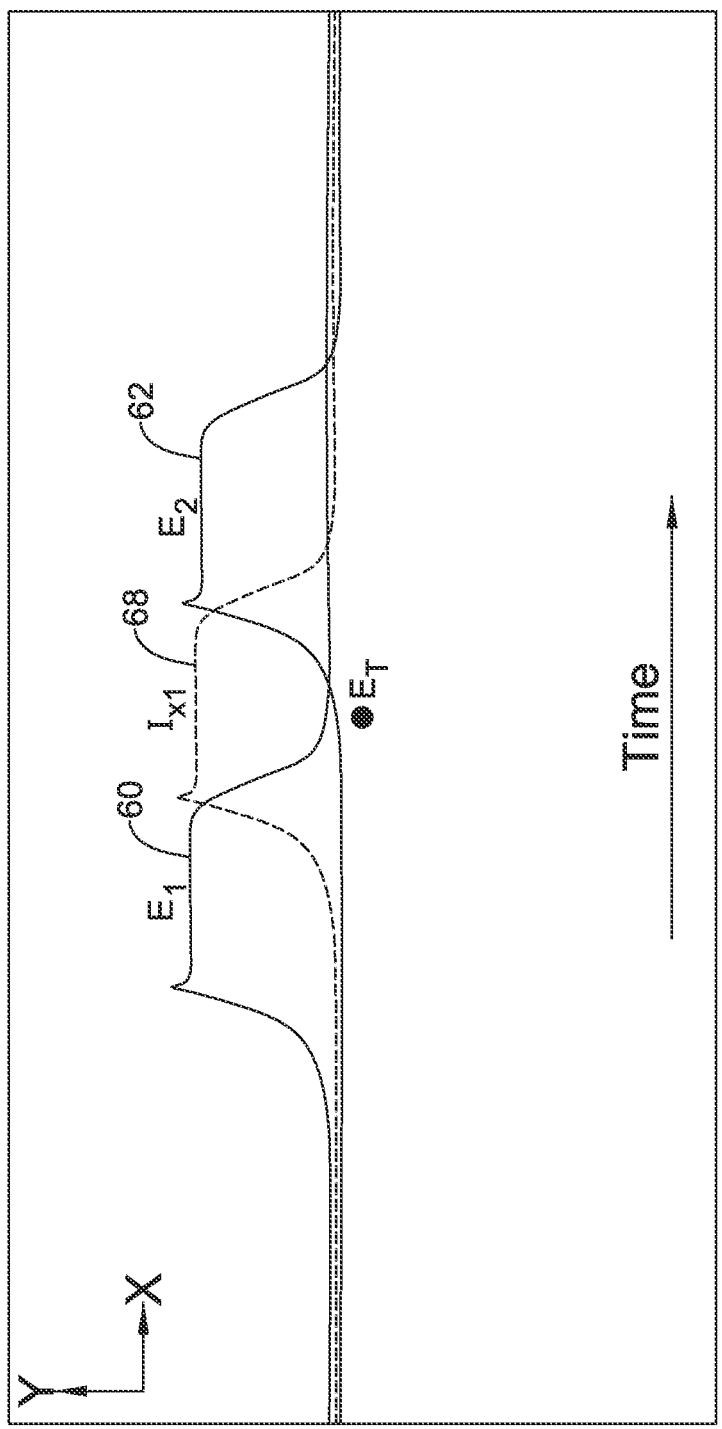
FIG. 11 is an illustration of two example electrogram curves and an example intermediate signal.

FIG. 11 illustrates an example beginning step to determine a target signal by interpolating a first latency, a second latency, a third latency and a fourth latency. It is contemplated that processor 32 may also be able to determine a target signal by interpolating a first latency, a second latency, a third latency and a fourth latency. Similarly to that discussed above, example electrodes E1 and E2 may sense and collect the voltage potential of a cellular wavefront excitation occurring as a wavefront moves underneath E1 and E2, respectively. Electrode E2 may sense the wavefront at a later point in time as compared to E1. Therefore, a latency will exist between the sensing of the excitation wavefront by E1 and E2.

Cardiac action potentials may fire at predictable rates. Consequently, cardiac cellular excitation signals may propagate at predictable velocities. Additionally, the position of electrodes E1 and E2 relative to each other may be known if they are located on a constellation catheter or similar sensing device. Therefore, knowing the relative positions of E1 and E2 relative to one another and the velocity of the excitation wavefront as it propagates underneath E1 and E2, the latency between E1 and E2 may be calculated. This example illustrates electrodes E1 and E2 aligned along the X axis. However, as stated above, it can be appreciated that the latency between two electrodes can be calculated in any direction for any wavefront excitation based on the summation of the vector components of the wavefront vector. Further, the latency at any point intermediate E1 and E2 may be calculated utilizing similar methodology. For example, the latency corresponding to the position of targeted electrode $E_T$ may be calculated. The following equation may be utilized in calculating the latency of targeted electrode $E_T$:

$$L_{X1} = x/dX * L_{12}$$

Once latency $L_{X1}$ is calculated, the electrogram signals sensed and collected at example electrodes E1 and E2 may be time shifted by a processor 32. Time shifting the signals at electrodes E1 and E2 may reduce the error which may be introduced if the signals were interpolated according to a method which does not take account of any latency effects. Therefore, in order to account for the latency effects inherent in cellular wavefront propagation, the example electrogram collected at E1 may be time shifted forward by latency $L_{X1}$ and electrode E2 may be time shifted backward by latency $L_{X1}$.

After time shifting the electogram signals at E1 and E2 by latency $L_{X1}$, the resultant signals may be averaged by processor 32 to calculate an intermediate signal $I_{x1}$ 68. The contribution of electrogram signals (sensed and collected at electrodes E1 and E2, for example) to the intermediate signal $I_{x1}$ 68 may be weighted according to their theoretical position relative to a final target signal. For example, it may be desired to interpolate an electrogram signal at a theoretical electrode $E_T$ positioned closer to E1. In that case, the "contribution" of the signal collected at E1 may be directly proportionate to its distance from $E_T$. The following equation may be utilized in calculating the weighted-average signal of E1 and E2, identified as $I_{x1}$ 68 and labeled as such in FIG. 11:

$$I_{X1}(t) = (1-x/dX) * E1(t-L_{X1}) + (x/dX) * (E2) * (t+L_{12}-L_{X1})$$

Figure 12:
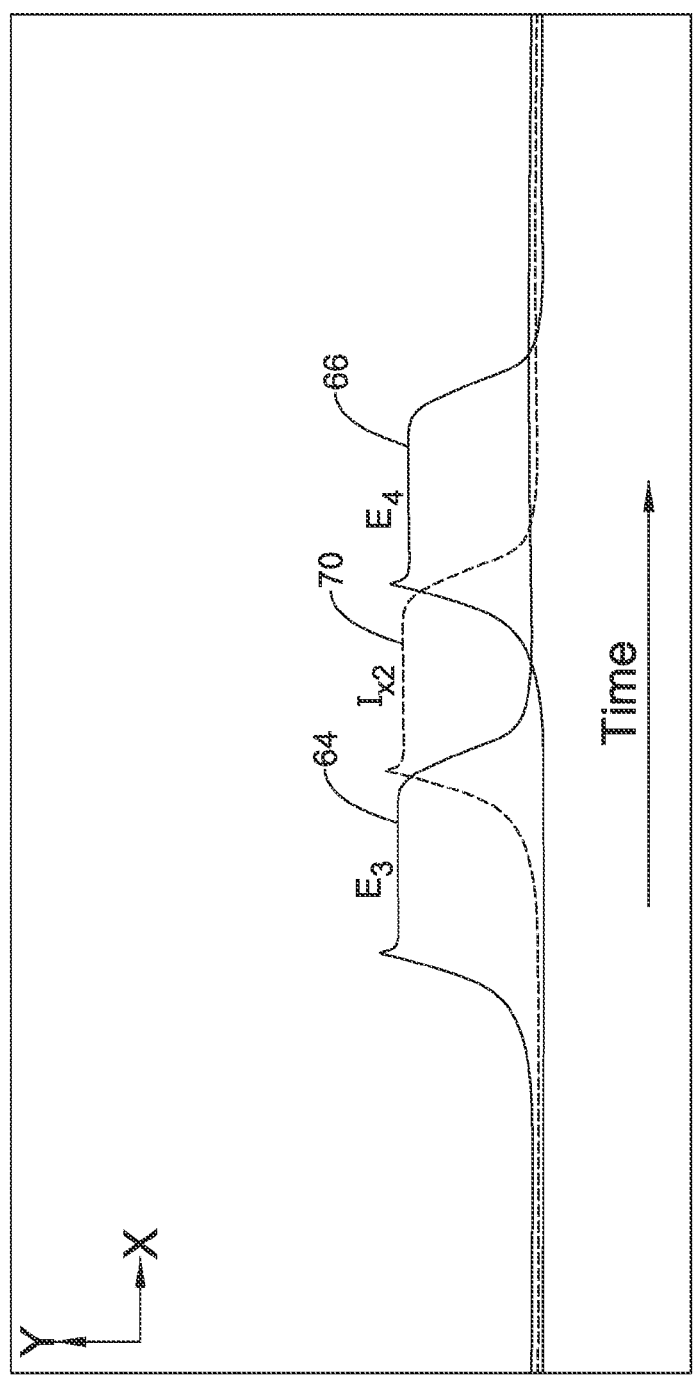
FIG. 12 is an illustration of two example electrogram curves and an example intermediate signal.

FIG. 12 illustrates the generation of an intermediate signal $I_{x2}$ 70 from electrogram signals E3 and E4 according to the method disclosed with respect to intermediate signal $I_{x1}$ 68. The following equation may be utilized in calculating the weighted-average signal of E3 and E4, identified as $I_{x2}$ and labeled as such in FIG. 12:

$$L_{X2} = X/dX * L_{34}$$

$$I_{X2}(t) = (1-x/dX) * E3(t-L_{X2}) + (x/dX) * (E4) * (t+L_{34}-L_{X2})$$

Figure 13:
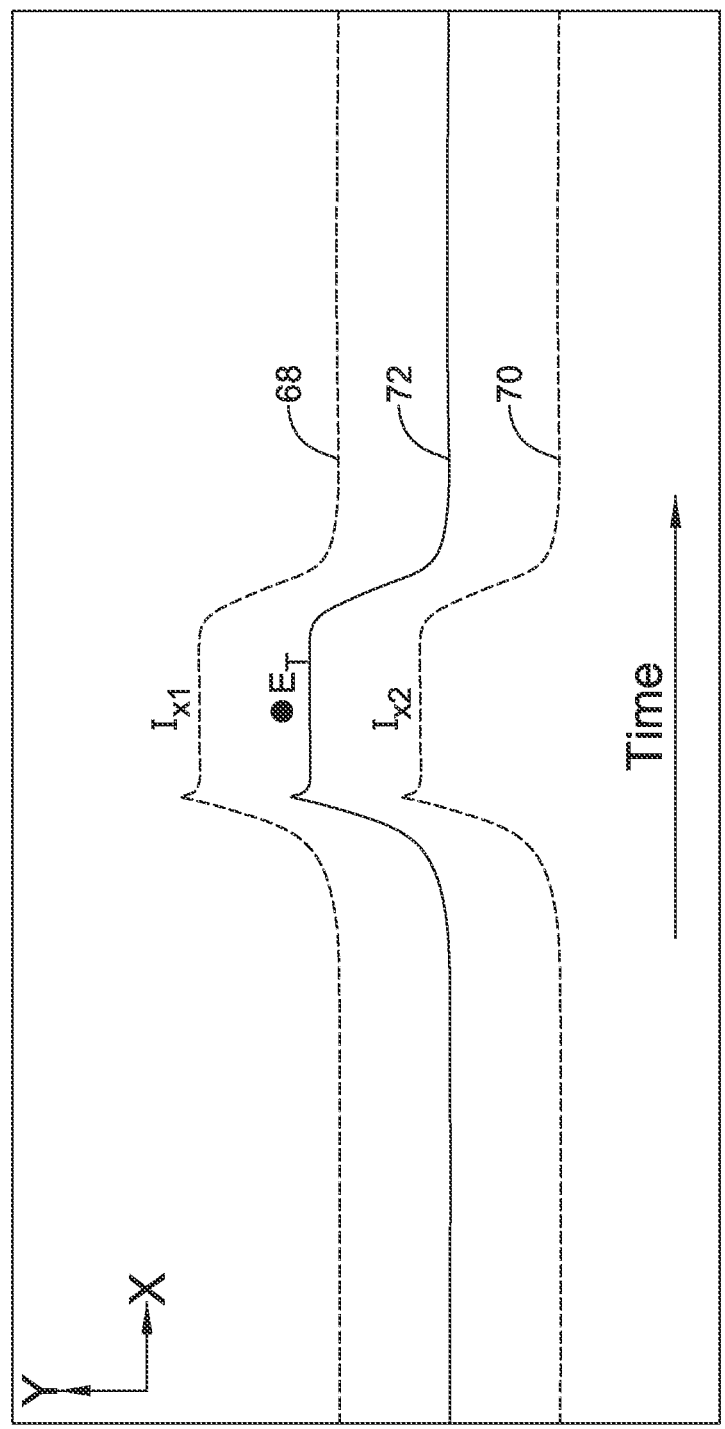
FIG. 13 is an illustration of two example intermediate signals and an example final interpolated electrogram signal.

FIG. 13 illustrates the generation of a final, interpolated signal 72 representing an electrogram signal at targeted electrode $E_T$. Similarly to the above discussion regarding calculating latencies in the X direction, latencies representing the time duration for a cellular excitation wavefront propagation to travel in the Y direction may be calculated. For example, the following equations may be utilized to calculate latencies of the targeted electrode $E_T$ in the Y direction between electrodes 1&3 and 2&4, respectfully:

$$L_{Y1} = y/dY * L_{13}$$

$$L_{Y2} = y/dY * L_{24}$$

In a method similar to that discussed relative to time shifting the signals along the X axis, to account for the latency effects in generating the interpolated signal for $E_T$, intermediate signals $I_{x1}$ and $I_{x2}$ may be time shifted in the Y direction. For example, intermediate signal $I_{x1}$ may be time shifted in the forward direction by latency $L_Y$. $L_Y$ may be calculated by the following equation:

$$L_Y = (1-x/dX) * L_{Y1} + (x/dX) * L_{Y2}$$

Similarly, intermediate signal $I_{x2}$ may be time shifted in the backward direction by latency $L_{GL}$. $L_{GL}$ may be calculated by the following equation:

$$L_{GL} = (1-X/dX) * L_{13}(x/dX) * L_{24}$$

To obtain the final, interpolated signal 72, the resultant time shifted intermediate signals $I_{x1}$ 68 and $I_{x2}$ 70 may be averaged by a processor 32. The intermediate signal $I_{x1}$ 68 may further be weighted according to its theoretical position relative to $I_{x1}$ 68 and $I_{x2}$ 70. For example, it may be desired to interpolate an electrogram signal at a theoretical electrode $E_T$ positioned closer to $I_{x1}$ 68, and therefore, the "contribution" of $I_{x1}$ 68 may be weighted as such. The following equation may be utilized in calculating the final interpolated signal 72 by taking the weighted-average of signals $I_{x1}$ 68 and $I_{x2}$ 70:

$$E_T(t) = (1-y/dY) * I_{x1}(t-L_Y) + (y/dY) * I_{x2}(t+L_{GL}-L_Y)$$

The above calculations are made in accordance with electrodes E1-E4 being positioned orthogonal to each other in an arbitrary coordinate system, indicated by X and Y directions. However, the positioning of electrodes E1-E4 within example X and Y coordinates is merely one example how they may be positioned relative to each other. This disclosure contemplates an interpolated signal may be generated from electrogram signals collected from numerous spatial relationships among multiple electrode pairs.

Further, in this disclosure, interpolation of target electrode $E_T$ was initiated along the X direction. Initiating the interpolation calculations along the X direction is merely a matter of convention. The method disclosed herein may be initiated along the Y (or any other) direction. Consequently, steps described in the X and Y directions in the disclosed examples may be interchanged, i.e. they would occur in the Y and X directions, respectively.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The invention's scope is, of course, defined in the language in which the appended claims are expressed.

What is claimed is:

1. A mapping medical device, comprising:
a catheter shaft with a plurality of electrodes coupled thereto, wherein each of the plurality of electrodes is configured to sense physiological signals and wherein the plurality of electrodes comprising a plurality of pairs of electrodes;

a processor configured to:
receive a plurality of physiological signals sensed by the plurality of electrodes;
receive a location of a theoretical electrode;
determine a latency for each of the plurality of pairs of electrodes;
calculate a plurality of latencies for the theoretical electrode, wherein each of the plurality of latencies for the theoretical electrode uses one of the determined latencies for the plurality of pairs of electrodes;
time shift each of the physiological signals using one of the plurality of calculated latencies;
combine the time-shifted physiological signals to determine an interpolated physiological signal at the location of the theoretical electrode, wherein the physiological signals are electrograms, and, wherein the interpolated physiological signal is an interpolated electrogram; and
output to a display device the interpolated physiological signal; and
a display device configured to display the interpolated physiological signal.

2. The medical device of claim 1,
wherein the plurality of electrodes comprises four electrodes; and
the plurality of pairs of electrodes comprises:
a first pair of electrodes including a first electrode and a second electrode of the plurality of electrodes, wherein the location of the theoretical electrode has a horizontal position that is between a horizontal position of the first electrode and a horizontal position of the second electrode on a horizontal axis;
a second pair of electrodes including a third electrode and a fourth electrode of the plurality of electrodes, wherein the location of the theoretical electrode has a horizontal position that is between a horizontal position of the third electrode and a horizontal position of the fourth electrode on the horizontal axis;
a third pair of electrodes including the first electrode and the third electrode, wherein the location of the theoretical electrode has a vertical position that is between a vertical position of the first electrode and a vertical position of the third electrode on a vertical axis; and
a fourth pair of electrodes including the second electrode and the fourth electrode, wherein the location of the theoretical electrode has a vertical position that is between a vertical position of the second electrode and a vertical position of the fourth electrode on the vertical axis.

3. The medical device of claim 2, wherein to combine the time shifted physiological signals, the processor is configured to:
determine a first intermediate signal using a time-shifted physiological signal of the first electrode and a time-shifted physiological signal of the second electrode;
determine a second intermediate signal using a time-shifted physiological signal of the third electrode and a time-shifted physiological signal of the fourth electrode; and
combine the first intermediate signal and the second intermediate signal.

4. The medical device of claim 3, wherein to combine the first intermediate signal and the second intermediate signal, the processor is configured to calculate a weighted average of the first intermediate signal and the second intermediate signal.

5. The medical device of claim 4, wherein to combine the time shifted physiological signals, the processor is configured to:
determine a third intermediate signal using a time-shifted physiological signal of the first electrode and a time-shifted physiological signal of the third electrode;
determine a fourth intermediate signal using a time-shifted physiological signal of the second electrode and a time-shifted physiological signal of the fourth electrode; and
combine the third intermediate signal and the fourth intermediate signal.

6. The medical device of claim 5, wherein to combine the third intermediate signal and the fourth intermediate signal, the processor is configured to calculate a weighted average of the third intermediate signal and the fourth intermediate signal.

7. The medical device of claim 6, wherein to combine the time shifted physiological signals, the processor is configured to combine the weighted average of the first intermediate signal and the second intermediate signal and the weighted average of the third intermediate signal and the fourth intermediate signal.

8. The medical device of claim 7, wherein to combine the weighted average of the first intermediate signal and the second intermediate signal and the weighted average of the third intermediate signal and the fourth intermediate signal, the processor is configured to calculate a weighted average of the weighted average of the first intermediate signal and the second intermediate signal and the weighted average of the third intermediate signal and the fourth intermediate signal.

9. The mapping medical device of claim 2,
wherein the plurality of calculated latencies for the theoretical electrode comprises a plurality of horizontal calculated latencies; and
wherein to time shift each of the physiological signals, the processor is configured to:
combine respective horizontal latencies to the first electrode, the second electrode, the third electrode, and the fourth electrode.

10. The mapping medical device of claim 2,
wherein the plurality of calculated latencies for the theoretical electrode comprises a plurality of vertical calculated latencies; and
wherein to time shift each of the physiological signals, the processor is configured to:
combine respective vertical latencies to the first electrode, the second electrode, the third electrode, and the fourth electrode.

11. A method for mapping an anatomical structure, the method comprising:
receiving a plurality of physiological signals sensed by a plurality of electrodes, wherein the plurality of electrodes comprising a plurality of pairs of electrodes;
receiving a location of a theoretical electrode;
determining a latency for each of the plurality of pairs of electrodes;
calculating a plurality of latencies for the theoretical electrode, wherein each of the plurality of latencies for the theoretical electrode uses one of the determined latencies for the plurality of pairs of electrodes;

time shifting each of the physiological signals using one of the plurality of calculated latencies;

combining the time-shifted physiological signals to determine an interpolated physiological signal at the location of the theoretical electrode, wherein the physiological signals are electrograms, and, wherein the interpolated physiological signal is an interpolated electrogram; and outputting to a display device the interpolated physiological signal.

12. The method of claim 11, wherein the plurality of electrodes comprises four electrodes; and the plurality of pairs of electrodes comprises:
- a first pair of electrodes including a first electrode and a second electrode of the plurality of electrodes, wherein the location of the theoretical electrode has a horizontal position that is between a horizontal position of the first electrode and a horizontal position of the second electrode on a horizontal axis;
- a second pair of electrodes including a third electrode and a fourth electrode of the plurality of electrodes, wherein the location of the theoretical electrode has a horizontal position that is between a horizontal position of the third electrode and a horizontal position of the fourth electrode on the horizontal axis;
- a third pair of electrodes including the first electrode and the third electrode, wherein the location of the theoretical electrode has a vertical position that is between a vertical position of the first electrode and a vertical position of the third electrode on a vertical axis; and
- a fourth pair of electrodes including the second electrode and the fourth electrode, wherein the location of the theoretical electrode has a vertical position that is between a vertical position of the second electrode and a vertical position of the fourth electrode on the vertical axis.

13. The method of claim 12, wherein combining the time shifted physiological signals comprises:
- determining a first intermediate signal using a time-shifted physiological signal of the first electrode and a time-shifted physiological signal of the second electrode;
- determining a second intermediate signal using a time-shifted physiological signal of the third electrode and a time-shifted physiological signal of the fourth electrode; and
- combining the first intermediate signal and the second intermediate signal.

14. The method of claim 13, wherein combining the first intermediate signal and the second intermediate signal comprises calculating a weighted average of the first intermediate signal and the second intermediate signal.

15. The method of claim 14, wherein combining the time shifted physiological signals comprises:
- determining a third intermediate signal using a time-shifted physiological signal of the first electrode and a time-shifted physiological signal of the third electrode;
- determining a fourth intermediate signal using a time-shifted physiological signal of the second electrode and a time-shifted physiological signal of the fourth electrode; and
- combining the third intermediate signal and the fourth intermediate signal.

16. The method of claim 15, wherein combining the third intermediate signal and the fourth intermediate signal comprises calculating a weighted average of the third intermediate signal and the fourth intermediate signal.

17. The method of claim 16, wherein combining the time shifted physiological signals comprises combining the weighted average of the first intermediate signal and the second intermediate signal and the weighted average of the third intermediate signal and the fourth intermediate signal.

18. The method of claim 17, wherein combining the weighted average of the first intermediate signal and the second intermediate signal and the weighted average of the third intermediate signal and the fourth intermediate signal comprises calculating a weighted average of the weighted average of the first intermediate signal and the second intermediate signal and the weighted average of the third intermediate signal and the fourth intermediate signal.

19. The method of claim 12, wherein the plurality of calculated latencies for the theoretical electrode comprises a plurality of horizontal calculated latencies; and wherein time shifting each of the physiological signals comprises:
- combining respective horizontal latencies to the first electrode, the second electrode, the third electrode, and the fourth electrode.

20. The method of claim 12, wherein the plurality of calculated latencies for the theoretical electrode comprises a plurality of vertical calculated latencies; and wherein time shifting each of the physiological signals comprises:
- combining respective vertical latencies to the first electrode, the second electrode, the third electrode, and the fourth electrode.

* * * * *